US008175681B2

(12) United States Patent
Hartmann et al.

(10) Patent No.: US 8,175,681 B2
(45) Date of Patent: May 8, 2012

(54) COMBINATION OF ELECTROMAGNETIC AND ELECTROPOTENTIAL LOCALIZATION

(75) Inventors: Steven L. Hartmann, Superior, CO (US); Andrew Bzostek, Erie, CO (US); Bradley A. Jascob, Broomfield, CO (US)

(73) Assignee: Medtronic Navigation Inc., Louisville, CO (US)

( * ) Notice: Subject to any disclaimer, the term of this patent is extended or adjusted under 35 U.S.C. 154(b) by 635 days.

(21) Appl. No.: 12/336,085

(22) Filed: Dec. 16, 2008

(65) Prior Publication Data

US 2010/0152571 A1    Jun. 17, 2010

(51) Int. Cl.
*A61B 5/05* (2006.01)
*A61B 19/00* (2006.01)

(52) U.S. Cl. .................. 600/424; 600/427; 128/899
(58) Field of Classification Search .............. 600/424, 600/407, 427; 128/899; 607/122
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,837,347 A | 9/1974 | Tower |
| 3,868,565 A | 2/1975 | Kuipers |
| 3,941,127 A | 3/1976 | Froning |
| 3,983,474 A | 9/1976 | Kuipers |
| 3,995,623 A | 12/1976 | Blake et al. |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |

(Continued)

FOREIGN PATENT DOCUMENTS

CA          964149 A1    3/1975

(Continued)

OTHER PUBLICATIONS

"Prestige Cervical Disc System Surgical Technique", 12 pgs.

(Continued)

*Primary Examiner* — Michael Rozanski
(74) *Attorney, Agent, or Firm* — Harness, Dickey

(57) ABSTRACT

A navigation system or combination of navigation systems can be used to provide two or more types of navigation or modalities of navigation to navigate a single instrument. The single instrument can be positioned within the patient and tracked. For example, both an Electromagnetic (EM) and Electropotential (EP) navigation system can be used to navigate an instrument within a patient.

29 Claims, 8 Drawing Sheets

U.S. PATENT DOCUMENTS

| | | |
|---|---|---|
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,506,680 A | 3/1985 | Stokes |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,619,246 A | 10/1986 | Molgaard-Nielsen et al. |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,696,304 A | 9/1987 | Chin |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,801,297 A | 1/1989 | Mueller |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,035,246 A | 7/1991 | Heuvelmans et al. |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,076,285 A | 12/1991 | Hess et al. |
| 5,078,140 A | 1/1992 | Kwoh |
| 5,078,714 A | 1/1992 | Katims |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |

| | | | | | |
|---|---|---|---|---|---|
| 5,167,239 A | 12/1992 | Cohen et al. | 5,391,199 A | 2/1995 | Ben-Haim |
| 5,178,164 A | 1/1993 | Allen | 5,394,457 A | 2/1995 | Leibinger et al. |
| 5,178,621 A | 1/1993 | Cook et al. | 5,394,875 A | 3/1995 | Lewis et al. |
| 5,186,174 A | 2/1993 | Schlondorff et al. | 5,397,329 A | 3/1995 | Allen |
| 5,187,475 A | 2/1993 | Wagener et al. | 5,398,684 A | 3/1995 | Hardy |
| 5,188,126 A | 2/1993 | Fabian et al. | 5,399,146 A | 3/1995 | Nowacki et al. |
| 5,190,059 A | 2/1993 | Fabian et al. | 5,400,384 A | 3/1995 | Fernandes et al. |
| 5,193,106 A | 3/1993 | DeSena | 5,402,801 A | 4/1995 | Taylor |
| 5,197,476 A | 3/1993 | Nowacki et al. | 5,408,409 A | 4/1995 | Glassman et al. |
| 5,197,965 A | 3/1993 | Cherry et al. | 5,413,573 A | 5/1995 | Koivukangas |
| 5,198,768 A | 3/1993 | Keren | 5,417,210 A | 5/1995 | Funda et al. |
| 5,198,877 A | 3/1993 | Schulz | 5,419,325 A | 5/1995 | Dumoulin et al. |
| 5,207,688 A | 5/1993 | Carol | 5,423,334 A | 6/1995 | Jordan |
| 5,211,164 A | 5/1993 | Allen | 5,425,367 A | 6/1995 | Shapiro et al. |
| 5,211,165 A | 5/1993 | Dumoulin et al. | 5,425,382 A | 6/1995 | Golden et al. |
| 5,211,176 A | 5/1993 | Ishiguro et al. | 5,426,683 A | 6/1995 | O'Farrell, Jr. et al. |
| 5,212,720 A | 5/1993 | Landi et al. | 5,426,687 A | 6/1995 | Goodall et al. |
| 5,214,615 A | 5/1993 | Bauer | 5,427,097 A | 6/1995 | Depp |
| 5,219,351 A | 6/1993 | Teubner et al. | 5,429,132 A | 7/1995 | Guy et al. |
| 5,222,499 A | 6/1993 | Allen et al. | 5,433,198 A | 7/1995 | Desai |
| 5,224,049 A | 6/1993 | Mushabac | RE35,025 E | 8/1995 | Anderton |
| 5,228,442 A | 7/1993 | Imran | 5,437,277 A | 8/1995 | Dumoulin et al. |
| 5,230,338 A | 7/1993 | Allen et al. | 5,443,066 A | 8/1995 | Dumoulin et al. |
| 5,230,623 A | 7/1993 | Guthrie et al. | 5,443,489 A | 8/1995 | Ben-Haim |
| 5,233,990 A | 8/1993 | Barnea | 5,444,756 A | 8/1995 | Pai et al. |
| 5,237,996 A | 8/1993 | Waldman et al. | 5,445,144 A | 8/1995 | Wodicka et al. |
| 5,249,581 A | 10/1993 | Horbal et al. | 5,445,150 A | 8/1995 | Dumoulin et al. |
| 5,251,127 A | 10/1993 | Raab | 5,445,166 A | 8/1995 | Taylor |
| 5,251,635 A | 10/1993 | Dumoulin et al. | 5,446,548 A | 8/1995 | Gerig et al. |
| 5,253,647 A | 10/1993 | Takahashi et al. | 5,447,154 A | 9/1995 | Cinquin et al. |
| 5,255,680 A | 10/1993 | Darrow et al. | 5,448,610 A | 9/1995 | Yamamoto et al. |
| 5,257,636 A | 11/1993 | White | 5,453,686 A | 9/1995 | Anderson |
| 5,257,998 A | 11/1993 | Ota et al. | 5,456,718 A | 10/1995 | Szymaitis |
| 5,261,404 A | 11/1993 | Mick et al. | 5,457,641 A | 10/1995 | Zimmer et al. |
| 5,265,610 A | 11/1993 | Darrow et al. | 5,458,718 A | 10/1995 | Venkitachalam |
| 5,265,611 A | 11/1993 | Hoenig et al. | 5,464,446 A | 11/1995 | Dreessen et al. |
| 5,265,622 A | 11/1993 | Barbere | 5,469,847 A | 11/1995 | Zinreich et al. |
| 5,269,759 A | 12/1993 | Hernandez et al. | 5,478,341 A | 12/1995 | Cook et al. |
| 5,271,400 A | 12/1993 | Dumoulin et al. | 5,478,343 A | 12/1995 | Ritter |
| 5,273,025 A | 12/1993 | Sakiyama et al. | 5,480,422 A | 1/1996 | Ben-Haim |
| 5,274,551 A | 12/1993 | Corby, Jr. | 5,480,439 A | 1/1996 | Bisek et al. |
| 5,279,309 A | 1/1994 | Taylor et al. | 5,483,961 A | 1/1996 | Kelly et al. |
| 5,285,787 A | 2/1994 | Machida | 5,485,849 A | 1/1996 | Panescu et al. |
| 5,291,199 A | 3/1994 | Overman et al. | 5,487,391 A | 1/1996 | Panescu |
| 5,291,889 A | 3/1994 | Kenet et al. | 5,487,729 A | 1/1996 | Avellanet et al. |
| 5,295,483 A | 3/1994 | Nowacki et al. | 5,487,757 A | 1/1996 | Truckai et al. |
| 5,297,549 A | 3/1994 | Beatty et al. | 5,490,196 A | 2/1996 | Rudich et al. |
| 5,299,253 A | 3/1994 | Wessels | 5,494,034 A | 2/1996 | Schlondorff et al. |
| 5,299,254 A | 3/1994 | Dancer et al. | 5,503,416 A | 4/1996 | Aoki et al. |
| 5,299,288 A | 3/1994 | Glassman et al. | 5,512,920 A | 4/1996 | Gibson |
| 5,300,080 A | 4/1994 | Clayman et al. | 5,513,637 A | 5/1996 | Twiss et al. |
| 5,305,091 A | 4/1994 | Gelbart et al. | 5,514,146 A | 5/1996 | Lam et al. |
| 5,305,203 A | 4/1994 | Raab | 5,515,160 A | 5/1996 | Schulz et al. |
| 5,306,271 A | 4/1994 | Zinreich et al. | 5,517,990 A | 5/1996 | Kalfas et al. |
| 5,307,072 A | 4/1994 | Jones, Jr. | 5,522,874 A | 6/1996 | Gates |
| 5,309,913 A | 5/1994 | Kormos et al. | 5,531,227 A | 7/1996 | Schneider |
| 5,315,630 A | 5/1994 | Sturm et al. | 5,531,520 A | 7/1996 | Grimson et al. |
| 5,316,024 A | 5/1994 | Hirschi et al. | 5,542,938 A | 8/1996 | Avellanet et al. |
| 5,318,025 A | 6/1994 | Dumoulin et al. | 5,543,951 A | 8/1996 | Moehrmann |
| 5,320,111 A | 6/1994 | Livingston | 5,546,940 A | 8/1996 | Panescu et al. |
| 5,325,728 A | 7/1994 | Zimmerman et al. | 5,546,949 A | 8/1996 | Frazin et al. |
| 5,325,873 A | 7/1994 | Hirschi et al. | 5,546,951 A | 8/1996 | Ben-Haim |
| 5,329,944 A | 7/1994 | Fabian et al. | 5,551,429 A | 9/1996 | Fitzpatrick et al. |
| 5,330,485 A | 7/1994 | Clayman et al. | 5,558,091 A | 9/1996 | Acker et al. |
| 5,333,168 A | 7/1994 | Fernandes et al. | 5,566,681 A | 10/1996 | Manwaring et al. |
| 5,342,295 A | 8/1994 | Imran | 5,568,384 A | 10/1996 | Robb et al. |
| 5,353,795 A | 10/1994 | Souza et al. | 5,568,809 A | 10/1996 | Ben-haim |
| 5,353,800 A | 10/1994 | Pohndorf et al. | 5,571,083 A | 11/1996 | Lemelson |
| 5,353,807 A | 10/1994 | DeMarco | 5,572,999 A | 11/1996 | Funda et al. |
| 5,359,417 A | 10/1994 | Muller et al. | 5,573,533 A | 11/1996 | Strul |
| 5,368,030 A | 11/1994 | Zinreich et al. | 5,575,794 A | 11/1996 | Walus et al. |
| 5,371,778 A | 12/1994 | Yanof et al. | 5,575,798 A | 11/1996 | Koutrouvelis |
| 5,375,596 A | 12/1994 | Twiss et al. | 5,583,909 A | 12/1996 | Hanover |
| 5,377,678 A | 1/1995 | Dumoulin et al. | 5,588,430 A | 12/1996 | Bova et al. |
| 5,383,454 A | 1/1995 | Bucholz | 5,590,215 A | 12/1996 | Allen |
| 5,385,146 A | 1/1995 | Goldreyer | 5,592,939 A | 1/1997 | Martinelli |
| 5,385,148 A | 1/1995 | Lesh et al. | 5,595,193 A | 1/1997 | Walus et al. |
| 5,386,828 A | 2/1995 | Owens et al. | 5,596,228 A | 1/1997 | Anderton et al. |
| 5,389,101 A | 2/1995 | Heilbrun et al. | 5,600,330 A | 2/1997 | Blood |

| Patent Number | Date | Inventor(s) | Patent Number | Date | Inventor(s) |
|---|---|---|---|---|---|
| 5,603,318 A | 2/1997 | Heilbrun et al. | 5,803,089 A | 9/1998 | Ferre et al. |
| 5,611,025 A | 3/1997 | Lorensen et al. | 5,807,252 A | 9/1998 | Hassfeld et al. |
| 5,617,462 A | 4/1997 | Spratt | 5,810,008 A | 9/1998 | Dekel et al. |
| 5,617,857 A | 4/1997 | Chader et al. | 5,810,728 A | 9/1998 | Kuhn |
| 5,619,261 A | 4/1997 | Anderton | 5,810,735 A | 9/1998 | Halperin et al. |
| 5,622,169 A | 4/1997 | Golden et al. | 5,820,553 A | 10/1998 | Hughes |
| 5,622,170 A | 4/1997 | Schulz | 5,823,192 A | 10/1998 | Kalend et al. |
| 5,627,873 A | 5/1997 | Hanover et al. | 5,823,958 A | 10/1998 | Truppe |
| 5,628,315 A | 5/1997 | Vilsmeier et al. | 5,828,725 A | 10/1998 | Levinson |
| 5,630,431 A | 5/1997 | Taylor | 5,828,770 A | 10/1998 | Leis et al. |
| 5,636,644 A | 6/1997 | Hart et al. | 5,829,444 A | 11/1998 | Ferre et al. |
| 5,638,819 A | 6/1997 | Manwaring et al. | 5,831,260 A | 11/1998 | Hansen |
| 5,639,276 A | 6/1997 | Weinstock et al. | 5,833,608 A | 11/1998 | Acker |
| 5,640,170 A | 6/1997 | Anderson | 5,834,759 A | 11/1998 | Glossop |
| 5,642,395 A | 6/1997 | Anderton et al. | 5,836,954 A | 11/1998 | Heilbrun et al. |
| 5,643,268 A | 7/1997 | Vilsmeier et al. | 5,840,024 A | 11/1998 | Taniguchi et al. |
| 5,645,065 A | 7/1997 | Shapiro et al. | 5,840,025 A | 11/1998 | Ben-Haim |
| 5,646,524 A | 7/1997 | Gilboa | 5,843,076 A | 12/1998 | Webster, Jr. et al. |
| 5,647,361 A | 7/1997 | Damadian | 5,848,967 A | 12/1998 | Cosman |
| 5,662,111 A | 9/1997 | Cosman | 5,851,183 A | 12/1998 | Bucholz |
| 5,664,001 A | 9/1997 | Tachibana et al. | 5,865,846 A | 2/1999 | Bryan et al. |
| 5,674,296 A | 10/1997 | Bryan et al. | 5,868,674 A | 2/1999 | Glowinski et al. |
| 5,676,673 A | 10/1997 | Ferre et al. | 5,868,675 A | 2/1999 | Henrion et al. |
| 5,681,260 A | 10/1997 | Ueda et al. | 5,871,445 A | 2/1999 | Bucholz |
| 5,682,886 A | 11/1997 | Delp et al. | 5,871,455 A | 2/1999 | Ueno |
| 5,682,890 A | 11/1997 | Kormos et al. | 5,871,487 A | 2/1999 | Warner et al. |
| 5,690,108 A | 11/1997 | Chakeres | 5,873,822 A | 2/1999 | Ferre et al. |
| 5,694,945 A | 12/1997 | Ben-Haim | 5,882,304 A | 3/1999 | Ehnholm et al. |
| 5,695,500 A | 12/1997 | Taylor et al. | 5,884,410 A | 3/1999 | Prinz |
| 5,695,501 A | 12/1997 | Carol et al. | 5,889,834 A | 3/1999 | Vilsmeier et al. |
| 5,696,500 A | 12/1997 | Diem | 5,891,034 A | 4/1999 | Bucholz |
| 5,697,377 A | 12/1997 | Wittkampf | 5,891,157 A | 4/1999 | Day et al. |
| 5,702,406 A | 12/1997 | Vilsmeier et al. | 5,904,691 A | 5/1999 | Barnett et al. |
| 5,711,299 A | 1/1998 | Manwaring et al. | 5,907,395 A | 5/1999 | Schulz et al. |
| 5,713,946 A | 2/1998 | Ben-Haim | 5,913,820 A | 6/1999 | Bladen et al. |
| 5,715,822 A | 2/1998 | Watkins et al. | 5,916,193 A | 6/1999 | Stevens et al. |
| 5,715,836 A | 2/1998 | Kliegis et al. | 5,920,395 A | 7/1999 | Schulz |
| 5,718,241 A | 2/1998 | Ben-Haim et al. | 5,921,992 A | 7/1999 | Costales et al. |
| 5,727,552 A | 3/1998 | Ryan | 5,923,727 A | 7/1999 | Navab |
| 5,727,553 A | 3/1998 | Saad | 5,928,248 A | 7/1999 | Acker |
| 5,729,129 A | 3/1998 | Acker | 5,935,160 A | 8/1999 | Auricchio et al. |
| 5,730,129 A | 3/1998 | Darrow et al. | 5,938,603 A | 8/1999 | Ponzi |
| 5,730,130 A | 3/1998 | Fitzpatrick et al. | 5,938,694 A | 8/1999 | Jaraczewski et al. |
| 5,732,703 A | 3/1998 | Kalfas et al. | 5,944,022 A | 8/1999 | Nardella et al. |
| 5,735,278 A | 4/1998 | Hoult et al. | 5,947,980 A | 9/1999 | Jensen et al. |
| 5,738,096 A | 4/1998 | Ben-Haim | 5,947,981 A | 9/1999 | Cosman |
| 5,740,802 A | 4/1998 | Nafis et al. | 5,950,629 A | 9/1999 | Taylor et al. |
| 5,740,808 A | 4/1998 | Panescu et al. | 5,951,475 A | 9/1999 | Gueziec et al. |
| 5,741,214 A | 4/1998 | Ouchi et al. | 5,951,571 A | 9/1999 | Audette |
| 5,742,394 A | 4/1998 | Hansen | 5,954,647 A | 9/1999 | Bova et al. |
| 5,744,953 A | 4/1998 | Hansen | 5,954,796 A | 9/1999 | McCarty et al. |
| 5,748,767 A | 5/1998 | Raab | 5,957,844 A | 9/1999 | Dekel et al. |
| 5,749,362 A | 5/1998 | Funda et al. | 5,964,796 A | 10/1999 | Imran |
| 5,749,835 A | 5/1998 | Glantz | 5,967,980 A | 10/1999 | Ferre et al. |
| 5,752,513 A | 5/1998 | Acker et al. | 5,967,982 A | 10/1999 | Barnett |
| 5,755,725 A | 5/1998 | Druais | 5,968,047 A | 10/1999 | Reed |
| RE35,816 E | 6/1998 | Schulz | 5,971,997 A | 10/1999 | Guthrie et al. |
| 5,758,667 A | 6/1998 | Slettenmark | 5,976,156 A | 11/1999 | Taylor et al. |
| 5,762,064 A | 6/1998 | Polvani | 5,980,535 A | 11/1999 | Barnett et al. |
| 5,767,669 A | 6/1998 | Hansen et al. | 5,983,126 A | 11/1999 | Wittkampf |
| 5,767,699 A | 6/1998 | Bosnyak et al. | 5,987,349 A | 11/1999 | Schulz |
| 5,767,960 A | 6/1998 | Orman | 5,987,960 A | 11/1999 | Messner et al. |
| 5,769,789 A | 6/1998 | Wang et al. | 5,999,837 A | 12/1999 | Messner et al. |
| 5,769,843 A | 6/1998 | Abela et al. | 5,999,840 A | 12/1999 | Grimson et al. |
| 5,769,861 A | 6/1998 | Vilsmeier | 6,001,130 A | 12/1999 | Bryan et al. |
| 5,772,594 A | 6/1998 | Barrick | 6,004,269 A | 12/1999 | Crowley et al. |
| 5,775,322 A | 7/1998 | Silverstein et al. | 6,006,126 A | 12/1999 | Cosman |
| 5,776,064 A | 7/1998 | Kalfas et al. | 6,006,127 A | 12/1999 | Van Der Brug et al. |
| 5,782,765 A | 7/1998 | Jonkman | 6,009,349 A | 12/1999 | Mouchawar et al. |
| 5,787,886 A | 8/1998 | Kelly et al. | 6,013,087 A | 1/2000 | Adams et al. |
| 5,792,055 A | 8/1998 | McKinnon | 6,014,580 A | 1/2000 | Blume et al. |
| 5,795,294 A | 8/1998 | Luber et al. | 6,016,439 A | 1/2000 | Acker |
| 5,797,849 A | 8/1998 | Vesely et al. | 6,019,725 A | 2/2000 | Vesely et al. |
| 5,799,055 A | 8/1998 | Peshkin et al. | 6,024,695 A | 2/2000 | Taylor et al. |
| 5,799,099 A | 8/1998 | Wang et al. | 6,050,267 A | 4/2000 | Nardella et al. |
| 5,800,352 A | 9/1998 | Ferre et al. | 6,050,724 A | 4/2000 | Schmitz et al. |
| 5,800,407 A | 9/1998 | Eldor | 6,059,718 A | 5/2000 | Taniguchi et al. |
| 5,800,535 A | 9/1998 | Howard, III | 6,063,022 A | 5/2000 | Ben-Haim |
| 5,802,719 A | 9/1998 | O'Farrell, Jr. et al. | 6,071,288 A | 6/2000 | Carol et al. |

| | | | | | | |
|---|---|---|---|---|---|---|
| 6,073,043 | A | 6/2000 | Schneider | 6,569,160 B1 | 5/2003 | Goldin et al. |
| 6,076,008 | A | 6/2000 | Bucholz | 6,574,498 B1 | 6/2003 | Gilboa |
| 6,088,527 | A | 7/2000 | Rybczynski | 6,584,174 B2 | 6/2003 | Schubert et al. |
| 6,090,105 | A | 7/2000 | Zepeda et al. | 6,593,884 B1 | 7/2003 | Gilboa et al. |
| 6,096,050 | A | 8/2000 | Audette | 6,595,989 B1 | 7/2003 | Schaer |
| 6,104,944 | A | 8/2000 | Martinelli | 6,602,271 B2 | 8/2003 | Adams et al. |
| 6,112,111 | A | 8/2000 | Glantz | 6,609,022 B2 | 8/2003 | Vilsmeier et al. |
| 6,118,845 | A | 9/2000 | Simon et al. | 6,611,141 B1 | 8/2003 | Schulz et al. |
| 6,122,538 | A | 9/2000 | Sliwa, Jr. et al. | 6,611,700 B1 | 8/2003 | Vilsmeier et al. |
| 6,122,541 | A | 9/2000 | Cosman et al. | 6,640,128 B2 | 10/2003 | Vilsmeier et al. |
| 6,122,552 | A | 9/2000 | Tockman et al. | 6,694,162 B2 | 2/2004 | Hartlep |
| 6,131,396 | A | 10/2000 | Duerr et al. | 6,701,176 B1 | 3/2004 | Halperin et al. |
| 6,139,183 | A | 10/2000 | Graumann | 6,701,179 B1 | 3/2004 | Martinelli et al. |
| 6,147,480 | A | 11/2000 | Osadchy et al. | 6,711,429 B1 | 3/2004 | Gilboa et al. |
| 6,149,592 | A | 11/2000 | Yanof et al. | 6,714,806 B2 | 3/2004 | Iaizzo et al. |
| 6,152,946 | A | 11/2000 | Broome et al. | 6,725,080 B2 | 4/2004 | Melkent et al. |
| 6,156,067 | A | 12/2000 | Bryan et al. | 6,868,195 B2 | 3/2005 | Fujita |
| 6,161,032 | A | 12/2000 | Acker | 6,888,623 B2 | 5/2005 | Clements |
| 6,165,181 | A | 12/2000 | Heilbrun et al. | 6,892,090 B2 | 5/2005 | Verard et al. |
| 6,167,296 | A | 12/2000 | Shahidi | 6,892,091 B1 | 5/2005 | Ben-Haim et al. |
| 6,172,499 | B1 | 1/2001 | Ashe | 6,950,689 B1 | 9/2005 | Willis et al. |
| 6,175,756 | B1 | 1/2001 | Ferre et al. | 6,990,370 B1 | 1/2006 | Beatty et al. |
| 6,178,345 | B1 | 1/2001 | Vilsmeier et al. | 7,020,522 B1 | 3/2006 | Hoijer et al. |
| 6,183,444 | B1 | 2/2001 | Glines et al. | 7,047,073 B2 | 5/2006 | Hoijer et al. |
| 6,192,280 | B1 | 2/2001 | Sommer et al. | 7,130,700 B2 | 10/2006 | Gardeski et al. |
| 6,194,639 | B1 | 2/2001 | Botella et al. | 7,189,208 B1 | 3/2007 | Beatty et al. |
| 6,196,230 | B1 | 3/2001 | Hall et al. | 7,207,989 B2 | 4/2007 | Pike, Jr. et al. |
| 6,201,387 | B1 | 3/2001 | Govari | 7,215,430 B2 | 5/2007 | Kacyra et al. |
| 6,203,493 | B1 | 3/2001 | Ben-Haim | 7,263,397 B2 | 8/2007 | Hauck et al. |
| 6,203,497 | B1 | 3/2001 | Dekel et al. | 7,305,121 B2 | 12/2007 | Kaufmann et al. |
| 6,207,111 | B1 | 3/2001 | Weinberg | 7,369,901 B1 | 5/2008 | Morgan et al. |
| 6,210,362 | B1 | 4/2001 | Ponzi | 7,421,300 B2 | 9/2008 | Smits et al. |
| 6,211,666 | B1 | 4/2001 | Acker | 7,479,141 B2 | 1/2009 | Kleen et al. |
| 6,213,995 | B1 | 4/2001 | Steen et al. | 7,570,791 B2 | 8/2009 | Frank et al. |
| 6,216,027 | B1 | 4/2001 | Willis et al. | 7,599,730 B2 | 10/2009 | Hunter et al. |
| 6,223,067 | B1 | 4/2001 | Vilsmeier et al. | 7,697,972 B2 | 4/2010 | Verard et al. |
| 6,226,543 | B1 | 5/2001 | Gilboa et al. | 7,715,604 B2 | 5/2010 | Sun et al. |
| 6,233,476 | B1 | 5/2001 | Strommer et al. | 7,988,639 B2 | 8/2011 | Starks |
| 6,236,875 | B1 | 5/2001 | Bucholz et al. | 2001/0007918 A1 | 7/2001 | Vilsmeier et al. |
| 6,236,886 | B1 | 5/2001 | Cherepenin et al. | 2001/0031920 A1 | 10/2001 | Kaufman et al. |
| 6,246,231 | B1 | 6/2001 | Ashe | 2001/0036245 A1 | 11/2001 | Kienzle et al. |
| 6,246,468 | B1 | 6/2001 | Dimsdale | 2002/0045810 A1 | 4/2002 | Ben-Haim |
| 6,253,770 | B1 | 7/2001 | Acker et al. | 2002/0049375 A1 | 4/2002 | Strommer et al. |
| 6,256,121 | B1 | 7/2001 | Lizotte et al. | 2002/0077544 A1 | 6/2002 | Shahidi |
| 6,259,942 | B1 | 7/2001 | Westermann et al. | 2002/0077568 A1 | 6/2002 | Haddock |
| 6,273,896 | B1 | 8/2001 | Franck et al. | 2002/0095081 A1 | 7/2002 | Vilsmeier et al. |
| 6,285,902 | B1 | 9/2001 | Kienzle, III et al. | 2002/0111662 A1 | 8/2002 | Iaizzo et al. |
| 6,298,262 | B1 | 10/2001 | Franck et al. | 2002/0128565 A1 | 9/2002 | Rudy |
| 6,301,498 | B1 | 10/2001 | Greenberg et al. | 2002/0147488 A1 | 10/2002 | Doan et al. |
| 6,314,310 | B1 | 11/2001 | Ben-Haim et al. | 2002/0183817 A1 | 12/2002 | Van Venrooij et al. |
| 6,330,356 | B1 | 12/2001 | Sundareswaran et al. | 2002/0193686 A1 | 12/2002 | Gilboa |
| 6,332,089 | B1 | 12/2001 | Acker et al. | 2003/0018251 A1 | 1/2003 | Solomon |
| 6,341,231 | B1 | 1/2002 | Ferre et al. | 2003/0028118 A1 | 2/2003 | Dupree et al. |
| 6,351,659 | B1 | 2/2002 | Vilsmeier | 2003/0055324 A1 | 3/2003 | Wasserman |
| 6,379,302 | B1 | 4/2002 | Kessman et al. | 2003/0074011 A1 | 4/2003 | Gilboa et al. |
| 6,381,485 | B1 | 4/2002 | Hunter et al. | 2003/0078494 A1 | 4/2003 | Panescu et al. |
| 6,389,187 | B1 | 5/2002 | Greenaway et al. | 2003/0108853 A1 | 6/2003 | Chosack et al. |
| 6,423,009 | B1 | 7/2002 | Downey et al. | 2003/0114908 A1 | 6/2003 | Flach |
| 6,424,856 | B1 | 7/2002 | Vilsmeier et al. | 2003/0225434 A1 | 12/2003 | Glantz et al. |
| 6,427,314 | B1 | 8/2002 | Acker | 2003/0231789 A1 | 12/2003 | Willis et al. |
| 6,428,547 | B1 | 8/2002 | Vilsmeier et al. | 2004/0001075 A1 | 1/2004 | Balakrishnan et al. |
| 6,434,415 | B1 | 8/2002 | Foley et al. | 2004/0024309 A1 | 2/2004 | Ferre et al. |
| 6,437,567 | B1 | 8/2002 | Schenck et al. | 2004/0044295 A1 | 3/2004 | Reinert et al. |
| 6,445,943 | B1 | 9/2002 | Ferre et al. | 2004/0064159 A1 | 4/2004 | Hoijer et al. |
| 6,447,504 | B1 | 9/2002 | Ben-Haim et al. | 2004/0068312 A1 | 4/2004 | Sigg et al. |
| 6,470,205 | B2 | 10/2002 | Bosselmann et al. | 2004/0070582 A1 | 4/2004 | Smith et al. |
| 6,470,207 | B1 | 10/2002 | Simon et al. | 2004/0097805 A1 | 5/2004 | Verard et al. |
| 6,474,341 | B1 | 11/2002 | Hunter et al. | 2004/0097806 A1 | 5/2004 | Hunter et al. |
| 6,478,802 | B2 | 11/2002 | Kienzle, III et al. | 2004/0162599 A1 | 8/2004 | Kurth |
| 6,484,049 | B1 | 11/2002 | Seeley et al. | 2004/0215298 A1 | 10/2004 | Richardson et al. |
| 6,490,475 | B1 | 12/2002 | Seeley et al. | 2004/0228453 A1 | 11/2004 | Dobbs et al. |
| 6,493,573 | B1 | 12/2002 | Martinelli et al. | 2004/0236395 A1 | 11/2004 | Iaizzo et al. |
| 6,493,575 | B1 | 12/2002 | Kesten et al. | 2004/0249281 A1 | 12/2004 | Olstad |
| 6,498,944 | B1 | 12/2002 | Ben-Haim et al. | 2004/0249430 A1 | 12/2004 | Martinez et al. |
| 6,499,488 | B1 | 12/2002 | Hunter et al. | 2004/0254437 A1 | 12/2004 | Hauck et al. |
| 6,516,046 | B1 | 2/2003 | Frohlich et al. | 2005/0018888 A1 | 1/2005 | Zonneveld |
| 6,527,443 | B1 | 3/2003 | Vilsmeier et al. | 2005/0119550 A1 | 6/2005 | Serra et al. |
| 6,546,270 | B1 | 4/2003 | Goldin et al. | 2005/0143651 A1 | 6/2005 | Verard et al. |
| 6,551,325 | B2 | 4/2003 | Neubauer et al. | 2005/0177151 A1 | 8/2005 | Coen et al. |

| | | |
|---|---|---|
| 2005/0187432 A1 | 8/2005 | Hale et al. |
| 2005/0245803 A1 | 11/2005 | Glenn Jr. et al. |
| 2006/0013523 A1 | 1/2006 | Childers et al. |
| 2006/0058604 A1 | 3/2006 | Avinash et al. |
| 2006/0117773 A1 | 6/2006 | Street et al. |
| 2006/0135883 A1 | 6/2006 | Jonsson et al. |
| 2006/0153468 A1 | 7/2006 | Solf et al. |
| 2006/0173268 A1 | 8/2006 | Mullick et al. |
| 2006/0200049 A1 | 9/2006 | Leo et al. |
| 2006/0206157 A1 | 9/2006 | Hoijer |
| 2006/0229513 A1 | 10/2006 | Wakai |
| 2006/0229594 A1 | 10/2006 | Francischelli et al. |
| 2006/0247520 A1 | 11/2006 | McGee |
| 2007/0016084 A1 | 1/2007 | Denault |
| 2007/0038052 A1 | 2/2007 | Swoyer et al. |
| 2007/0043413 A1 | 2/2007 | Eversull et al. |
| 2007/0046661 A1 | 3/2007 | Ma et al. |
| 2007/0049817 A1 | 3/2007 | Preiss et al. |
| 2007/0112388 A1 | 5/2007 | Salo |
| 2007/0123944 A1 | 5/2007 | Zdeblick |
| 2007/0135721 A1 | 6/2007 | Zdeblick |
| 2007/0135803 A1 | 6/2007 | Belson |
| 2007/0156019 A1 | 7/2007 | Larkin et al. |
| 2007/0164900 A1 | 7/2007 | Schneider et al. |
| 2007/0167801 A1 | 7/2007 | Webler et al. |
| 2007/0252074 A1 | 11/2007 | Ng et al. |
| 2007/0270682 A1 | 11/2007 | Huang et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0015466 A1 | 1/2008 | Lerman |
| 2008/0024493 A1 | 1/2008 | Bordoloi et al. |
| 2008/0038197 A1 | 2/2008 | John et al. |
| 2008/0058656 A1 | 3/2008 | Costello et al. |
| 2008/0071142 A1 | 3/2008 | Gattani et al. |
| 2008/0118117 A1 | 5/2008 | Gauldie et al. |
| 2008/0132800 A1 | 6/2008 | Hettrick et al. |
| 2008/0183072 A1 | 7/2008 | Robertson et al. |
| 2008/0207997 A1 | 8/2008 | Higgins et al. |
| 2008/0221438 A1 | 9/2008 | Chen et al. |
| 2008/0243025 A1 | 10/2008 | Holmstrom et al. |
| 2008/0249375 A1 | 10/2008 | Obel |
| 2009/0017430 A1 | 1/2009 | Muller-Daniels et al. |
| 2009/0063118 A1 | 3/2009 | Dachille et al. |
| 2009/0093857 A1 | 4/2009 | Markowitz et al. |
| 2009/0099619 A1 | 4/2009 | Lessmeier et al. |
| 2009/0103793 A1 | 4/2009 | Borland et al. |
| 2009/0126575 A1 | 5/2009 | Son et al. |
| 2009/0129477 A1 | 5/2009 | Yang |
| 2009/0131955 A1 | 5/2009 | Wenderow et al. |
| 2009/0192381 A1 | 7/2009 | Brockway et al. |
| 2009/0227861 A1 | 9/2009 | Ganatra et al. |
| 2009/0253976 A1 | 10/2009 | Harlev et al. |
| 2009/0253985 A1 | 10/2009 | Shachar et al. |
| 2009/0262109 A1 | 10/2009 | Markowitz et al. |
| 2009/0262979 A1 | 10/2009 | Markowitz et al. |
| 2009/0262980 A1 | 10/2009 | Markowitz et al. |
| 2009/0262982 A1 | 10/2009 | Markowitz et al. |
| 2009/0262992 A1 | 10/2009 | Markowitz et al. |
| 2009/0264727 A1 | 10/2009 | Markowitz et al. |
| 2009/0264738 A1 | 10/2009 | Markowitz et al. |
| 2009/0264739 A1 | 10/2009 | Markowitz et al. |
| 2009/0264740 A1 | 10/2009 | Markowitz et al. |
| 2009/0264741 A1 | 10/2009 | Markowitz et al. |
| 2009/0264742 A1 | 10/2009 | Markowitz et al. |
| 2009/0264743 A1 | 10/2009 | Markowitz et al. |
| 2009/0264744 A1 | 10/2009 | Markowitz et al. |
| 2009/0264745 A1 | 10/2009 | Markowitz et al. |
| 2009/0264746 A1 | 10/2009 | Markowitz et al. |
| 2009/0264747 A1 | 10/2009 | Markowitz et al. |
| 2009/0264748 A1 | 10/2009 | Markowitz et al. |
| 2009/0264749 A1 | 10/2009 | Markowitz et al. |
| 2009/0264750 A1 | 10/2009 | Markowitz et al. |
| 2009/0264751 A1 | 10/2009 | Markowitz et al. |
| 2009/0264752 A1 | 10/2009 | Markowitz et al. |
| 2009/0264777 A1 | 10/2009 | Markowitz et al. |
| 2009/0264778 A1 | 10/2009 | Markowitz et al. |
| 2009/0265128 A1 | 10/2009 | Markowitz et al. |
| 2009/0267773 A1 | 10/2009 | Markowitz et al. |
| 2009/0281417 A1 | 11/2009 | Hartmann et al. |
| 2009/0297001 A1 | 12/2009 | Markowitz et al. |
| 2010/0004724 A1 | 1/2010 | Markowitz et al. |
| 2010/0022873 A1 | 1/2010 | Hunter et al. |
| 2010/0030061 A1 | 2/2010 | Canfield et al. |
| 2010/0030063 A1 | 2/2010 | Lee et al. |
| 2010/0030298 A1 | 2/2010 | Martens et al. |
| 2010/0152571 A1 | 6/2010 | Hartmann et al. |
| 2010/0210938 A1 | 8/2010 | Verard et al. |
| 2011/0054293 A1 | 3/2011 | Markowitz et al. |
| 2011/0054304 A1 | 3/2011 | Markowitz et al. |

FOREIGN PATENT DOCUMENTS

| | | |
|---|---|---|
| DE | 3042343 A1 | 6/1982 |
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 T0 | 11/2002 |
| EP | 0062941 | 10/1982 |
| EP | 0119660 A1 | 9/1984 |
| EP | 0155857 | 9/1985 |
| EP | 0319844 | 6/1989 |
| EP | 0326768 A2 | 8/1989 |
| EP | 0350996 A1 | 1/1990 |
| EP | 363117 | 4/1990 |
| EP | 0419729 A1 | 4/1991 |
| EP | 0427358 | 5/1991 |
| EP | 0456103 | 11/1991 |
| EP | 0581704 A1 | 2/1994 |
| EP | 0651968 A1 | 5/1995 |
| EP | 0655138 A1 | 5/1995 |
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 1393674 A1 | 3/2004 |
| EP | 1421913 A1 | 5/2004 |
| EP | 2136706 | 12/2009 |
| FR | 2417970 A1 | 9/1979 |
| FR | 2618211 | 1/1989 |
| GB | 2094590 A | 9/1982 |
| GB | 2164856 A | 4/1986 |
| JP | 62327 | 6/1983 |
| JP | 63240851 A | 10/1988 |
| JP | 2765738 T | 4/1991 |
| JP | 3267054 | 11/1991 |
| JP | 6194639 | 7/1994 |
| WO | WO-8809151 A1 | 12/1988 |
| WO | WO-8905123 | 6/1989 |
| WO | WO-9005494 A1 | 5/1990 |
| WO | WO-9103982 A1 | 4/1991 |
| WO | WO-9104711 A1 | 4/1991 |
| WO | WO-9107726 A1 | 5/1991 |
| WO | WO-9203090 A1 | 3/1992 |
| WO | WO-9206645 A1 | 4/1992 |
| WO | WO-9404938 A1 | 3/1994 |
| WO | WO-9423647 A1 | 10/1994 |
| WO | WO-9424933 A1 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 A1 | 3/1998 |
| WO | WO-9838908 A1 | 9/1998 |
| WO | WO-9848722 A1 | 11/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9927839 A2 | 6/1999 |

| | | | |
|---|---|---|---|
| WO | WO-9929253 A1 | 6/1999 | |
| WO | WO-9933406 A1 | 7/1999 | |
| WO | WO-9937208 A1 | 7/1999 | |
| WO | WO-9938449 A1 | 8/1999 | |
| WO | WO-9952094 A1 | 10/1999 | |
| WO | WO-9960939 A1 | 12/1999 | |
| WO | WO-0006701 A1 | 2/2000 | |
| WO | WO-0035531 A1 | 6/2000 | |
| WO | WO-0130437 A1 | 5/2001 | |
| WO | WO-0134050 A2 | 5/2001 | |
| WO | WO-0187136 A2 | 11/2001 | |
| WO | WO-02064011 A2 | 8/2002 | |
| WO | WO-02064040 A2 | 8/2002 | |
| WO | WO-2005112836 A2 | 12/2005 | |
| WO | WO-2006042039 A2 | 4/2006 | |
| WO | WO-2006117773 A1 | 11/2006 | |
| WO | WO-2007067945 | 6/2007 | |
| WO | WO-2007111542 A1 | 10/2007 | |
| WO | WO-2007136451 A2 | 11/2007 | |
| WO | WO-2008108901 | 9/2008 | |
| WO | WO-2008147961 A1 | 12/2008 | |
| WO | WO-2009126575 A1 | 10/2009 | |
| WO | WO-2009129477 A1 | 10/2009 | |
| WO | WO-2010074986 A1 | 7/2010 | |

OTHER PUBLICATIONS

"Vital Images Receives 510(k) Clearance to Market VScore(TM) With AutoGate(TM); Breakthrough in Cardiac CT Imaging Simplifies Screening for Heart Disease," Press Release. Vital Images, Inc., Feb. 6, 2001 (4 pages).

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bergstrom et al. Stereotaxic Computed Tomography, Am. J. Roentgenol, vol. 127 pp. 167-170 (1976).

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Brown, R., M.D., A Stereotactic Head Frame for Use with CT Body Scanners, Investigative Radiology .COPYRGT. J.B. Lippincott Company, pp. 300-304 (Jul.-Aug. 1979).

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.

Bucholz, R.D., et al. Image-guided surgical techniques for infections and trauma of the central nervous system, Neurosurg. Clinics of N.A., vol. 7, No. 2, pp. 187-200 (1996).

Bucholz, R.D., et al., A Comparison of Sonic Digitizers Versus Light Emitting Diode-Based Localization, Interactive Image-Guided Neurosurgery, Chapter 16, pp. 179-200 (1993).

Bucholz, R.D., et al., Intraoperative localization using a three dimensional optical digitizer, SPIE—The Intl. Soc. for Opt. Eng., vol. 1894, pp. 312-322 (Jan. 17-19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics andComputer-Assisted Surgery, Grenoble, France, pp. 459-466 (Mar. 19-22, 1997).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254-263.

Cinquin et al., "Computer Assisted Medical Interventions," International Advanced Robotics Programme, Sep. 1989, pp. 63-65.

Clarysse et al., "A Computer-Assisted System for 3-D Frameless Localization in Stereotaxic MRI," IEEE Transactions on Medical Imaging, vol. 10, No. 4, Dec. 1991, pp. 523-529.

Cutting M.D. et al., Optical Tracking of Bone Fragments During Craniofacial Surgery, Second Annual International Symposium on Medical Robotics and Computer Assisted Surgery, pp. 221-225, (Nov. 1995).

European Search Report completed Mar. 1, 2004 for European application EP03024327, claiming benefit of U.S. Appl. No. 10/299,969, filed Nov. 19, 2002.

European Search Report completed Sep. 29, 2004 for European application EP04016056, claiming benefit of U.S. Appl. No. 10/619,216, filed Jul. 14, 2003.

Feldmar et al., "3D-2D Projective Registration of Free-Form Curves and Surfaces," Rapport de recherche (Inria Sophia Antipolis), 1994, pp. 1-44.

Foley et al., "Fundamentals of Interactive Computer Graphics," The Systems Programming Series, Chapter 7, Jul. 1984, pp. 245-266.

Foley et al., "Image-guided Intraoperative Spinal Localization," Intraoperative Neuroprotection, Chapter 19, 1996, pp. 325-340.

Foley, "The SteathStation: Three-Dimensional Image-Interactive Guidance for the Spine Surgeon," Spinal Frontiers, Apr. 1996, pp. 7-9.

Friets, E.M., et al. A Frameless Stereotaxic Operating Microscope for Neurosurgery, IEEE Trans. on Biomed. Eng., vol. 36, No. 6, pp. 608-617 (Jul. 1989).

Gallen, C.C., et al., Intracranial Neurosurgery Guided by Functional Imaging, Surg. Neurol., vol. 42, pp. 523-530 (1994).

Galloway, R.L., et al., Interactive Image-Guided Neurosurgery, IEEE Trans. on Biomed. Eng., vol. 89, No. 12, pp. 1226-1231 (1992).

Galloway, R.L., Jr. et al, Optical localization for interactive, image-guided neurosurgery, SPIE, vol. 2164 (May 1, 1994) pp. 137-145.

Germano, "Instrumentation, Technique and Technology", Neurosurgery, vol. 37, No. 2, Aug. 1995, pp. 348-350.

Gildenberg et al., "Calculation of Stereotactic Coordinates from the Computed Tomographic Scan," Neurosurgery, vol. 10, No. 5, May 1982, pp. 580-586.

Gomez, C.R., et al., Transcranial Doppler Ultrasound Following Closed Head Injury: Vasospasm or Vasoparalysis?, Surg. Neurol., vol. 35, pp. 30-35 (1991).

Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. '96, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13 (1994) pp. 193-211.

Hamadeh et al, "Kinematic Study of Lumbar Spine Using Functional Radiographies and 3D/2D Registration," TIMC UMR 5525—IMAG (1997).

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Intracardiac Echocardiographic Guidance & Monitoring During Percutaneous Endomyocardial Gene Injection in Porcine Heart, Seung, et al. (Human Gene Therapy 12:893-903 May 20, 2001).

Jacob, Al, et al., "A Whole-Body Registration-Free Navigation System for Image-Guided Surgery and Interventional Radiology," Investigative Radiology, vol. 35 No. 5 (May 2000) pp. 279-288.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51 (1996) pp. 635-638.

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. Car '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique for Accurate Transpedicular Screw Fixation Using CT Data and a 3-D Optical Localizer," TIMC, Faculte de Medecine de Grenoble. (1995).

Lavallee et al., "Image guided operating robot: a clinical application in stereotactic neurosurgery," Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11.sup.th Annual International Conference, 1989, pp. 0926-0927.

Lavallee, "VI Adaption de ja Methodologie a Quelques Applications Cliniques," Chapitre VI, pp. 133-148.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Cotonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al. "Computer Assisted Spine Surgery", Clinical Assisted Spine Surgery, No. 337, pp. 86-96, (Apr. 1997).

Muschlitz, Lin, "Ultrasound in the OR suite is providing more detailed information to allow less invasive surgeries." Technology—Ultra Sound Surgical Partners (Sep. 2003) Medical Imaging. http://www.imagingeconomics.com/issues/articles/M1_2003-09_03.asp (accessed on Aug. 12, 2010).

Ng, W.S. et al., Robotic Surgery—A First-Hand Experience in Transurethral Resection of the Prostate Surgery, IEEE Eng. in Med. and Biology, pp. 120-125 (Mar. 1993).

Partial European Search Report completed Mar. 1, 2004 for European application EP03024327, claiming benefit of U.S. Appl. No. 10/299,969, filed Nov. 19, 2002.

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12.sup.th International Conference, IPMI '91, Jul. 7-12, 136-141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Enffernung tiefliegender Gefa.beta.mi.beta.bildungen mit Hilfe der Sonar-Stereometrie (Microsurgical Removal of Deep-Seated Vascular Malformations Using Sonar Stereometry). Ultraschall in Med. 12, pp. 80-83(1991).

Reinhardt, Hans. F., Neuronavigation: A Ten-Year Review, Neurosurgery (1996) pp. 329-341.

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS (1995) pp. 185-192.

Smith et al., "Computer Methods for Improved Diagnostic Image Display Applied to Stereotactic Neurosurgery," Automedical, vol. 14, 1992, pp. 371-382.

Smith et al., "The Neurostation.TM.—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosuroy, vol. 79, pp. 296-303 (Aug. 1993).

The Laitinen Stereotactic System, E2-E6.

Thompson, et al., A System for Anatomical and Functional Mapping of the Human Thalamus, Computers and Biomedical Research, vol. 10, pp. 9-24 (1977).

Trobraugh, J.W., et al.; Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR vol. Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," Igaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," (1997) pp. 119-128.

"EnSite NavX™ Navigation & Visualization Technology." 3 pages, St. Jude Medical. http://www.sjmprofessional.com/Products/US/Mapping-and-Visualization/EnSite-NavX-Navigation-and-Visualization-Technology.aspx Web. Accessed Jun. 19, 2009.

"Local Lisa® Intracardiac Navigation System Model 9670000/9670025." Technical Manual Version 1.2, Chapter 1, pp. 1-19. 2004.

Brenner, David J., Ph.D., "Computed Tomography—An Increasing Source of Radiation Exposure", The New England Journal of Medicine (Nov. 29, 2007), pp. 2277-2284.

Gepstein, Lior, M.D., "A Novel Method for Nonfluoroscopic Catheter-Based Electroanatomical Mapping of the Heart, In Vitro and In Vivo Accuracy Results", American Heart Association, Learn and Live, Circulation (1997), http://circ.ahajournals.org/cgi/content/abstract/95/6/1611 printed Oct. 2, 2008.

International Preliminary Report on Patentability and Written Opinion for PCT/US2009/040998 mailed Oct. 28, 2010, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117549, filed May 8, 2008.

International Preliminary Report on Patentability and Written Opinion for PCT/US2009/0400984 mailed Oct. 28, 2010, claiming benefit of U.S. Appl. No. 12/117,549, filed May 8, 2008.

International Preliminary Report on Patentability and Written Opinion for PCT/US2009/040979 mailed Oct. 28, 2010 claiming benefit of U.S. Appl. No. 12/117,537, filed May 8, 2008.

International Preliminary Report on Patentability and Written Opinion mailed Oct. 29, 2009 for PCT/US2007/089087, of which U.S. Appl. No. 12/492,906 filed Jun. 26, 2009 claims benefit.

International Search Report and Written Opinion for PCT/US2008/088189 mailed Apr. 3, 2009, claiming benefit of U.S. Appl. No. 12/183,796, filed Jul. 31, 2008; and claims priority to U.S. Appl. No. 11/966382, filed Dec. 28, 2007.

International Search Report and Written Opinion for PCT/US2009/0400984 mailed Sep. 21, 2009, claiming benefit of U.S. Appl. No. 12/117,549, filed May 8, 2008.

International Search Report and Written Opinion for PCT/US2009/040998 mailed Jul. 29, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.

International Search Report and Written Opinion for PCT/US2009/067486 mailed May 4, 2010, claiming benefit of U.S. Appl. No. 12/336,085, filed Dec. 16, 2008.

International Search Report and Written Opinion mailed Dec. 6, 2010 for PCT/US2010/051248, which claims benefit of U.S. Appl. No. 12/609,734 filed Oct. 30, 2009.

International Search Report and Written Opinon for PCT/US2009/040979 mailed Sep. 21, 2009 claiming benefit of U.S. Appl. No. 12/117,537, filed May 8, 2008.

International Search Report for PCT/US2007/089087 mailed Jul. 9, 2008, of which U.S. Appl. No. 12/492,906 filed Jun. 26, 2009 claims benefit.

Invitation to Pay Additional Fees for PCT/US2009/0400984 mailed Jul. 30, 2009, claiming benefit of U.S. Appl. No. 12/117,549, filed May 8, 2008.

Invitation to Pay Additional Fees for PCT/US2009/040979 mailed Jul. 30, 2009 claiming benefit of U.S. Appl. No. 12/117,537, filed May 8, 2008.

Invitation to Pay Additional Fees for PCT/US2009/067486 mailed Mar. 5, 2010, claiming benefit of U.S. Appl. No. 12/336,085, filed Dec. 16, 2008.

Invitation to Pay Additional Fees for PCT/US2010/047241 mailed Jan. 10, 2011, claiming benefit of U.S. Appl. No. 12/844,065, filed Jul. 27, 2010.

Invitation to Pay Additional Fees mailed Jul. 7, 2010 for PCT/US2010/030534 claiming benefit of U.S. Appl. No. 12/421,375, filed Apr. 9, 2009.

Jiang, Yuan. "An Impedance-Based Catheter Poisitioning System for Cardiac Mapping and Navigation." IEEE Transactions on Biomedical Engineering, (Aug. 2009) pp. 1963-1970, vol. 56, No. 8.

Markowitz, Toby, et al., "Unleaded: The Fluoroless 3D Lead Implant", Presented at Heart Rhythm Society, Denver, CO, (May 2007) 1 pg.

Markowitz, Toby, et al., Abstract Submission, "Unleaded: The Fluoroless 3D Lead Implant", Mar. 2007 2 pgs.

Milstein, S. et al., "Initial Clinical Results of Non-Fluoroscopic Pacemaker Lead Implantation." (pre-presentation abstract) May 14-17, 2008. 2 pgs.

Milstein, S. et al., "Initial Clinical Results of Non-Fluoroscopic Pacemaker Lead Implantation." (poster presentation) May 14-17, 2008. 1 pg.

Nelder, J.A., et al. "A simplex method for function minimization." vol. 7, Issue 4, (1965) pp. 308-313.The Computer Journal.

Savage, George, M.D., "Electric Tomography (ET)—A Novel Method for Assessing Myocardial Motion and Cardiac Performance", Heart Rhythm Society, Denver, CO (May 9-12, 2007) 1 pg.

Wittkampf, Fred, H.M., et al., "LocaLisa: New Technique for Real-Time 3-Dimensional Localization of Regular Intracardiac Electrodes." Circulation Journal of the American Heart Association, 1999; 99; 13-12-1317.

Wittkampf, Fred., H.M., et al. "Accuracy of the LocaLisa System in Catheter Ablation Procedures." Journal of Electrocardiology vol. 32 Supplement (1999). Heart Lung Institute, University Hospital Utrecht, The Netherlands.

International Search Report and Written Opinion mailed May 4, 2010 for PCT/US2009/067486 claiming benefit of U.S. Appl. No. 12/336,085 filed Dec. 16, 2008.

Invitation to Pay Additional Fees mailed Mar. 5, 2010 for PCT/US2009/067486 claiming benefit of U.S. Appl. No. 12/336,085, filed Dec. 16, 2008.

Birkfellner, Wolfgang, et al. "Calibration of Tracking Systems in a Surgical Environment," IEEE Transactions on Medical Imaginge, IEEE Service Center, Piscataway, NJ, US, vol. 17, No. 5. (Oct. 1, 1998) XP011035767. ISSN: 0278-0062 the whole document.

Hubert-Tremblay, Vincent, et al. "Octree indexing of DICOM images for voxel number reduction and improvement of Monte Carolo simulation computing efficiency," Medical Physics, AIP, Melville, NY, US, vol. 33, No. 8, (Jul. 21, 2006) pp. 2819-2831, XP012092212, ISSN: 0094-2405, DOI: 10.1118/1.2214305 pp. 2820-2821.

International Preliminary Report on Patentability mailed Oct. 11, 2011 for PCT/US2010/030534 claming benefit of U.S. Appl. No. 12/421,375, filed Apr. 9, 2009.

International Search Report and Written Opinon mailed Jul. 25, 2011 for PCT/US2010/047241 claiming benefit of U.S. Appl. No. 12/844,065, filed Jul. 27, 2010.

International Search Report mailed Sep. 13, 2010 for PCT/US2010/030534 darning benefit of U.S. Appl. No. 12/421,375, filed Apr. 9, 2009.

Invitation to Pay Additional Fees mailed Jul. 7, 2010 for PCT/US2010/030534 darning benefit of U.S. Appl. No. 12/421,375, filed Apr. 9, 2009.

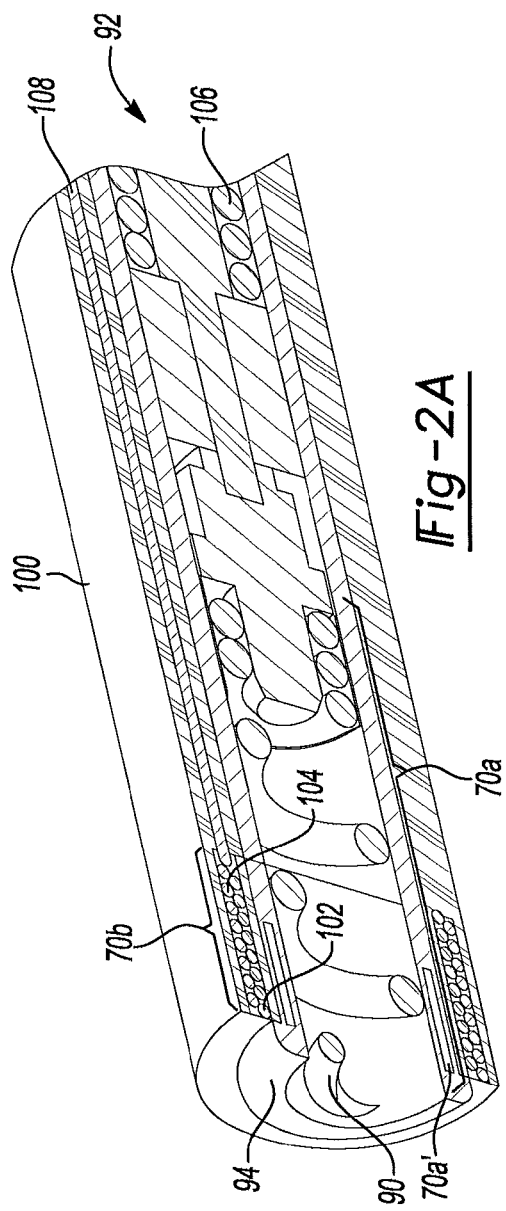
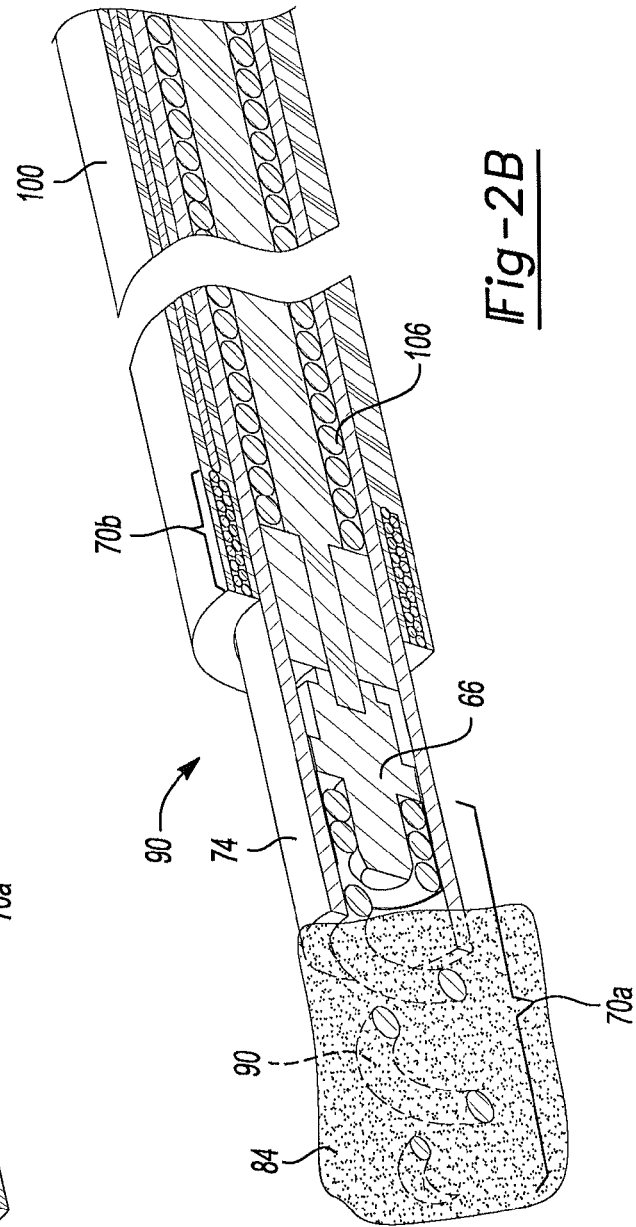
Fig-2A
Fig-2B

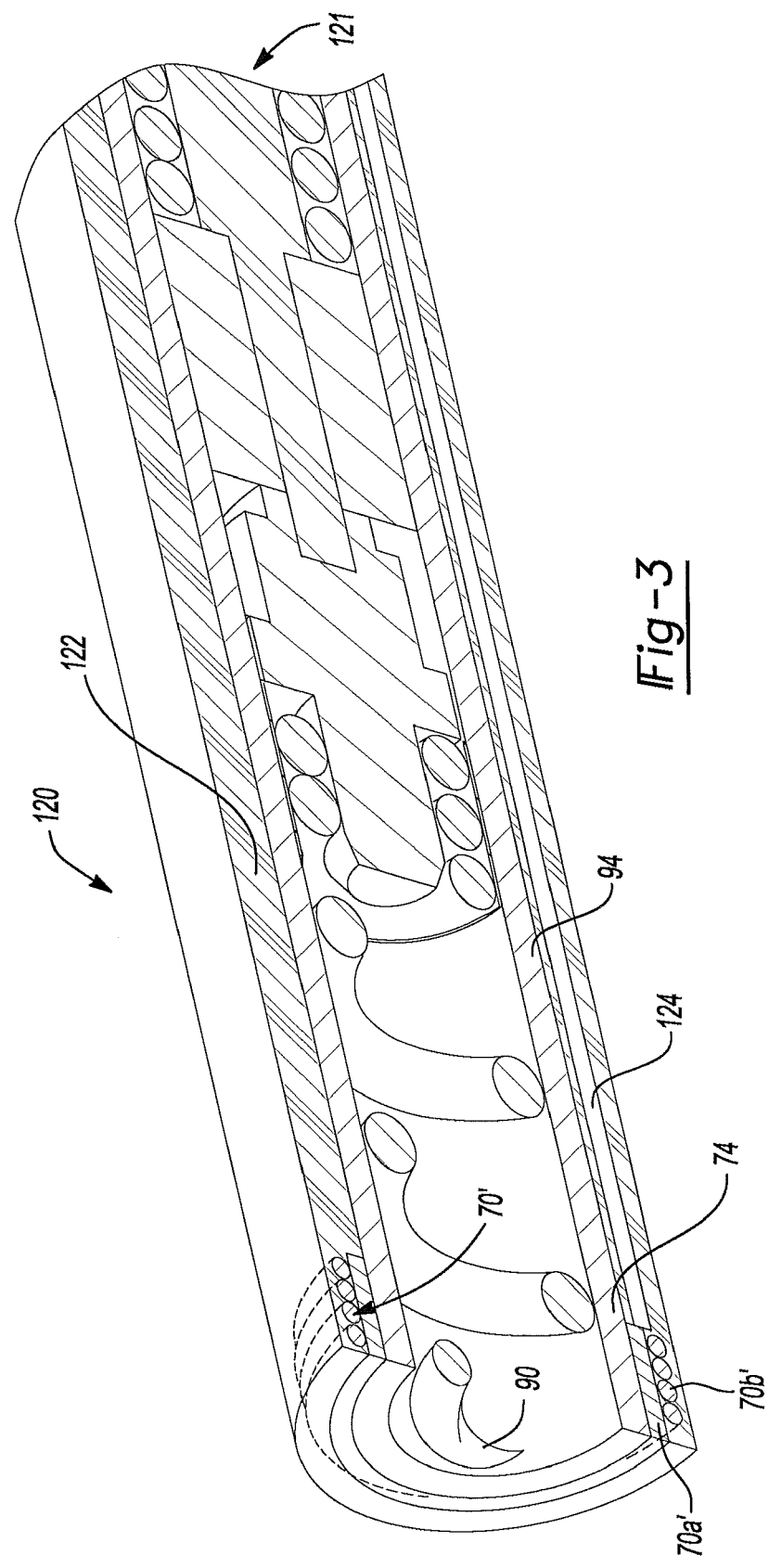

COMBINATION OF ELECTROMAGNETIC AND ELECTROPOTENTIAL LOCALIZATION

FIELD

The present disclosure relates generally to a system for localizing a tracked instrument, and particularly to a localization system using two or more modalities for localizing the instrument within a volume.

BACKGROUND

This section provides background information related to the present disclosure which is not necessarily prior art.

A navigation system can be used to track and navigate an instrument within a volume. For example, a navigation system can be used to track an instrument during a procedure, such as a surgical procedure. Various systems can be used to track instruments including electromagnetic systems, optical systems, acoustic systems, and other appropriate systems.

Tracking an instrument can allow for determination of a position of the instrument relative to the patient without directly viewing the instrument within the patient. Various methods can be used to achieve this result, such as directly tracking a particular portion of the instrument exterior to the patient or tracking a distal point of the instrument within the patient.

Differing navigation systems can be used to track different instruments within a patient. For example, a long substantially rigid instrument can be tracked with an optical navigation system that can track a proximal and/or end of the instrument that is external to the patient. Based on determinations, a position of a distal tip or an end of the instrument within the patient can be made. Additionally, navigation systems can use fields, such as electromagnetic fields, to track and navigate a distal portion of an instrument that is within a patient.

SUMMARY

This section provides a general summary of the disclosure, and is not a comprehensive disclosure of its full scope or all of its features.

A navigation system or combination of navigation systems can be used to provide two or more types of navigation or modalities of navigation to navigate a single instrument. The single instrument can be positioned within the patient and tracked. For example, both an Electromagnetic (EM) and Electropotential (EP) tracking systems can be used to navigate an instrument within a patient.

A navigation system can generally include a localizer and a tracking sensor. One skilled in the art will understand that the localizer can either transmit or receive a signal and the tracking sensor can also transmit or receive a signal to allow for a determination of a location of the tracking sensor associated with the surgical instrument. A surgical instrument can have associated therewith two or more tracking sensors that can be used in two or more modalities of navigation. For example, a surgical instrument may include an electrode that can be used with an EP tracking system and can also be associated or moved relative to a tracking sensor that includes an EM coil to be used with an EM tracking system.

An instrument can include one or more tracking sensors to be used with two or more navigation systems during a single procedure. In addition, a method can be used to register the two navigation systems during a single procedure. The registration of the two navigation systems can allow all or a selected number of points within one navigational domain to be coordinated or correlated to all or selected points in a second navigational domain. For example, a surgical instrument can include a single tracking sensor that can be tracked within two navigation modalities. Also, a surgical instrument with a single tracking sensor can be moved relative to a second tracking sensor, where each of the tracking sensors are tracked in different navigation modalities. According to various embodiments, when a first tracking sensor is positioned at a known location relative to a second tracking sensor, a navigation volume or domain of the first navigation system can be registered to a navigation volume or domain of a second navigation system. In this way, a first and second navigation system can be registered for navigating a tracking sensor or a surgical instrument within the two navigation modalities.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2A is a detailed cross-section view of an instrument, according to various embodiments;

FIG. 2B is a detailed cross-section and environmental view of an instrument, according to various embodiments;

FIG. 3 is a detailed cross-section view of an instrument, according to various embodiments;

Corresponding reference numerals indicate corresponding parts throughout the several views of the drawings.

DETAILED DESCRIPTION

Example embodiments will now be described more fully with reference to the accompanying drawings.

Figure 1:
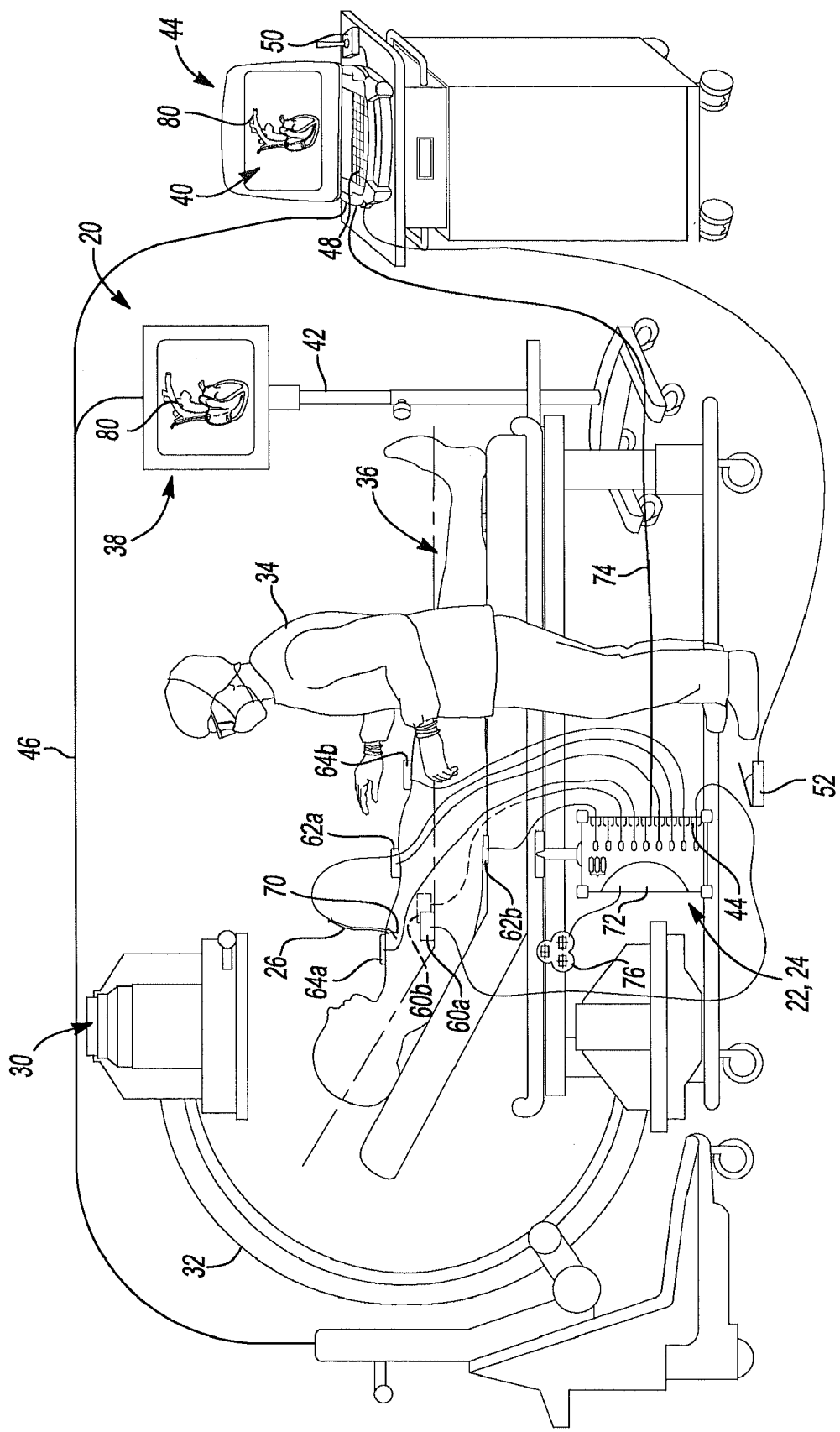
FIG. 1 is an environmental view of a navigation system.

A surgical navigation system 20 is illustrated in FIG. 1. A first tracking system can include an electropotential (EP) tracking system 22. A second tracking system can include an electromagnetic (EM) tracking system 24. Appropriate tracking systems can include those disclosed in U.S. patent application Ser. No. 12/117,537, filed on May 8, 2008 and U.S. Patent Publication No. 2004/0097805, published on May 20, 2004, both incorporated herein by reference. The first and second tracking systems 22, 24 can be used to track a surgical instrument 26. The surgical instrument 26 can be any appropriate instrument, including a lead used as a part of an implantable medical device (IMD) for heart rhythm treatment, neurological treatment, or other appropriate purposes.

The surgical navigation system 20 can also include other components, such as an imaging system 30. The imaging system 30 can be any appropriate imaging system and is exemplary illustrated as a fluoroscopic C-arm system 32.

Other imaging systems can include computed tomography (CT) imaging systems, magnetic resonance imaging (MRI) systems, and positron emission tomography (PET) imaging systems. The imaging systems 30 can be used by a surgeon 34 to image a patient 36 prior to (preoperatively), during (intraoperatively), or after (postoperatively) a procedure. Imaging the patient 36 can create image data that can be viewed on a display device 38 or a display device 40. The display device 38, 40 can be provided alone, such as on a stand 42 or with a processing system as a part of a workstation or processing system 44. The image data can be transferred from the imaging system 30 through a data transmission system 46, such as a wired or wireless transmission system, to the display devices 38, 40.

The navigation system 20, also including the tracking systems 22, 24 can be incorporated or connected to the processor system 44. The processor system 44 can include human input devices such as a keyboard 48, a joystick or mouse 50, a foot pedal 52 or any other appropriate human input device. Each of the human input devices 48-52 can be connected with the processor system 44 or other systems, such as the imaging system 30, for control or actuation thereof.

The EP tracking system 22 can include components to generate a current in the patient 36. The EP tracking system can include or be based on the Localisa™ intracardiac tracking system sold by Medtronic, Inc. have a place of business in Minneapolis, Minn. The EP tracking system 22 can also include portions disclosed in U.S. Pat. Nos. 5,697,377 or 5,983,126 to Wittkampf, incorporated herein by reference Briefly, the EP tracking system 22 can include a pair of axis electrodes, which can also be referred to as a localizer, operable to generate a current within a volume, such as the patient 36. The axis electrodes can include three pairs of axis electrodes to generate three substantially orthogonal axes of current within the patient 26 (also see FIG. 4). The axis electrodes can include a first pair 60a, 60b, a second pair 62a, 62b, and a third pair 64a, 64b. The axis can be defined by an alternating current that is generated between any pair of the axis electrodes. For example, the first pair of axis electrodes 60a and 60b can be positioned on a left and right side of the patient 36 to define an X-axis when a current is generated between the two axis electrodes 60a and 60b.

The substantially orthogonal axis of current can be used to determine or calculate a location of a tracking device 70. The tracking device 70 can include a first or EP tracking device 70a and a second or EM tracking device 70b. The EP tracking system 22 can be used to track the EP tracking device 70a. The first tracking device 70a can sense a voltage in the patient 36 based upon the induced current between any pair of the axis electrodes 60a-64b. The voltage can be related to a position of the first tracking device 70a in the patient 36.

The pairs of axis electrodes 60a-64b can be driven with a generator in a controller 72 that is connected via wires or wirelessly with the axis electrodes 60a-64b. The generator can provide the power to generate the alternating current in the patient 36 between the respective axis electrodes 60a-64b. The controller 72 can also include a connection for the instrument 26 to communicate a signal from the tracking device 70 to the controller. The connection with the instrument 26 can be wired or wireless, according to various embodiments. In addition, the controller 72 can include a processor portion or simply be a transmitter to transmit signals from the tracking device 70. Signals can be transmitted from the controller 72 to the processor system 44 with a transmission system 74. The transmission system 74 can be a wired or wireless transmission system.

The EM tracking system 24 can also be associated with the controller 72 or can be provided with a separate controller system. It will be understood that various separate circuitry portions may be provided in the controller 72 to generate or operate the EP tracking system 22 or the EM tracking system 24.

The EM tracking system 24 includes an EM localizer 76 that can be positioned relative to the patient 36. The EM tracking system can include the AxiEM™ electromagnetic tracking system sold by Medtronic Navigation, Inc. having a place of business in Colorado, USA. The localizer 76 can generate an electromagnetic field that is sensed by the EM tracking device 70b. Alternatively, the EM tracking device 70b can generate a field that is sensed by the localizer 76.

A localizer can be used as a part of a tracking system to determine the location of the tracking device 70. For example, the localizer 76 can be interconnected with the controller 72 to transmit a signal to the processor system 44 regarding the position of the EM tracking device 70b. The axis electrodes 60a-64b can be a localizer that induces axes of current in the patient 36 to localize the EP tracking device 70a. Accordingly, the localizer can refer to a portion of the tracking system which can be exterior to the volume, such as the patient 36, that is used to determine a position of the tracking device 70.

According to various embodiments, the localizer devices, including the EM localizer 76 and the axis electrodes 60a-64b, can be used to define a navigation domain in a patient space of the patient 36. Patient space can be the physical space that is being operated on during the operative procedure. The patient space can also include the navigated space through which the surgical instrument 26 is being navigated. Image space can be defined by image data 80 that is displayed on the display devices 38, 40. Image data 80 can include any appropriate image data, such as image data of a heart 84 (FIG. 4) of the patient 36. the image data 80 displayed on the display devices 38, 40 can also include atlas data. Atlas data can include statistical or historical data. The atlas data can be registered or morphed to the patient image data or patient space. It will be understood that atlas data may be used in an imageless navigation system. For example, an imageless navigation system may not require the acquisition of image data of the patient 36.

The patient space can be registered to the image space of the image data 80 according to any appropriate technique, including those discussed herein. Generally, however, the patient space is registered to the image data 80 to allow for displaying or a super imposing an icon or representation of a tracked device, for example the surgical instrument 26, over the image data 80 on the display device 38, 40. Registration generally allows for a transformation of the image data to the patient space. Various registration techniques can include contour matching, fiducial or point matching, automatic registration, or any other appropriate registration. For example, various landmarks or fiducials can be identified in the image data 80 and the same fiducials or landmarks can be identified in the patient 36, such as within the heart 84. The image data 80 can then be transformed to the patient space of the patient 36 so that a proper location of a superimposed icon 26i can be shown relative to the image data 80 of the heart 84. Registration techniques can include those discussed in the U.S. patent applications incorporated above. In addition, as discussed herein, the EP tracking system 22 can be registered to the EM tracking system 24. The registration of the EP tracking system 22 to the EM tracking system 24 can allow navigation of the EP tacking device 70a with the image data 80.

Turning to FIGS. 2A and 2B, the tracking device 70 can include the two tracking devices 70a and 70b. The first tracking device 70a can be a single electrode or a tip electrode 90 or ring electrode (not illustrated) of a lead assembly 92. The lead assembly 92 can be a lead for any appropriate device, such as a pacing or defibrillator system. The lead assembly 92 can be positioned or delivered within a sheath 94 according to generally known lead assemblies, such as the such as the Attain family of catheters sold by Medtronic Inc., having a place of business in Minneapolis, Minn.

The lead assembly 92 can be positioned within the patient 36, such as relative to the heart 84, with a catheter assembly 100. The catheter assembly 100 can be any appropriate configuration. The catheter 100 can include a body molded to substantially define a cannula. The catheter assembly 100 can include the second tracking device 70b. The second tracking device 70b can include a first coil 102 and a second coil 104, or any appropriate number of coils, as part of the EM tracking device 70b. The coils can be coiled with any appropriate configuration, such as around substantially orthogonal axes to one another. The second tracking device 70b, however, can sense an electromagnetic field generated with the localizer 76 or generate an electromagnetic field that is sensed by the localizer 76.

The two tracking devices 70a, 70b can be used with respective tracking systems 22, 24. The first tracking device 70a can sense a voltage or determine bioimpedance (such as an impedance of a tissue of the patient 36) because of the induced current from the axis electrodes 60a-64b. The inducement of the current generates a voltage that can be sensed with the EP tracking device 70a. The voltage sensed by the EP tracking device 70a can be transmitted to the controller 72 with an appropriate communication line, such as a conductor 106. The conductor 106 can be conductively coupled to the EP tracking device 70a. It will be understood that although the EP tracking device 70a is illustrated as the tip electrode 90 of the lead assembly 92, that the EP tracking device 70a can also include an alternative EP tracking device 70a' formed as a part of the sheath 94. Regardless of the position of the EP tracking device 70a, its contact (e.g. by removal of a portion of insulation around the electrode) with a conductive medium or electrolyte of the patient 36 can increase and provide efficiency of detecting an appropriate voltage. The voltage sensed by the EP tracking device 70a can be used to determine the position of the EP tracking device 70a as discussed further herein and also described in the above incorporated U.S. patent applications and patents.

The second tracking device 70b, according to various embodiments, can sense an electromagnetic field generated by the localizer 76. For example, a current can be induced in one or more of the coils 102, 104 that is dependent upon the position of the coils 102, 104 in a portion of the electromagnetic field. The generated current can be sent as a signal along a transmission line 108 to the controller 72.

As discussed further herein, and illustrated in FIG. 2B, the lead assembly 92 can be moved relative to tissue of the heart 84 to position the distal tip electrode 90 into the heart 84. When positioning the distal tip electrode 90 into the heart 84, the sheath 94 and the tip 90, which can include the first tracking device 70a, can move relative to the catheter assembly 100. Moving the first tracking device 70a relative to the catheter assembly 100 moves the first tracking device 70a relative to the second tracking device 70b. As discussed herein, this can be used to determine the location of the first tracking device 70a relative to the second tracking device 70b for registration of the EP tracking system 22 and the EM tracking system 24. This determination can be used to track the first tracking device 70a relative to the patient 36 and with the registered image data 80.

In addition, the tracking devices 70a and 70b could be the same coil of wire or conductive material provided with different insulation characteristics. For example, the loops or turns of the tracking device 70a can be electrically separated from the loops or turns of wire for the second tracking device 70b. Both sets of loops can be of the same length of wire over top one another. The conductive media or loops of the first tracking device 70a can be external and exposed to the patient to sense or measure the voltage in the patient. The second portion of the loops can be isolated from the patient and insulated, but they can, along with the first portion, sense the field of the EM tracking system 24.

Turning to FIG. 3, an instrument 120, according to various embodiments, is illustrated. The instrument 120 can include a lead assembly 121 substantially similar to the lead assembly 92 discussed above, including a tip electrode 90 and a sheath 94. The instrument 120 can also include a catheter assembly 122. The lead assembly 121, including the distal tip 90 and the sheath 94 can be moved relative to the catheter assembly 122.

The catheter assembly 122 can include the tracking device 70' as a single unit or device including an EP tracking device 70a' and one or more windings of an EM tracking device 70b'. The EM tracking device 70b' can be positioned substantially over or around the EP tracking device 70a'. The EP tracking device 70a' can include an annular ring that is molded into or formed with the catheter assembly 122. The EP tracking device 70a' can be used with the EP tracking system 22 similar to the distal tip electrode 90 of the lead assembly 92. The EM tracking device 70b' can be used with the EM tracking system 24 similar to the windings 102, 104 of the EM tracking device 70b. Nevertheless, the EP tracking device 70a' and the EM tracking device 70b' can be positioned substantially atop one another. This allows for the tracked position of the EP tracking device 70a' and the tracked position of the EM tracking device 70b' to be substantially coincident throughout a tracked procedure. A signal from either of the EP tracking device 70a' or the EM tracking device 70b' can be transmitted along or with a communication system 124, which can include a wired or wireless transmission system.

Again, it will be understood, that the tracking device 70' can be tracked with the two tracking systems 22, 24. As discussed above, the electrode of the EP tracking device 70a' can sense a voltage within the patient 36. The EM tracking device 70b' can sense a magnetic field or electromagnetic field or transmit a magnetic field or electromagnetic field. Accordingly, the single tracking device 70' can be used with two or more tracking systems 22, 24 to determine a location of the tracking device 70' and the catheter and lead assembly 120. It will be further understood that the tip electrode 90 of the lead assembly 121 can also be used as the EP tracking device with the EP tracking system 22.

Figure 4:
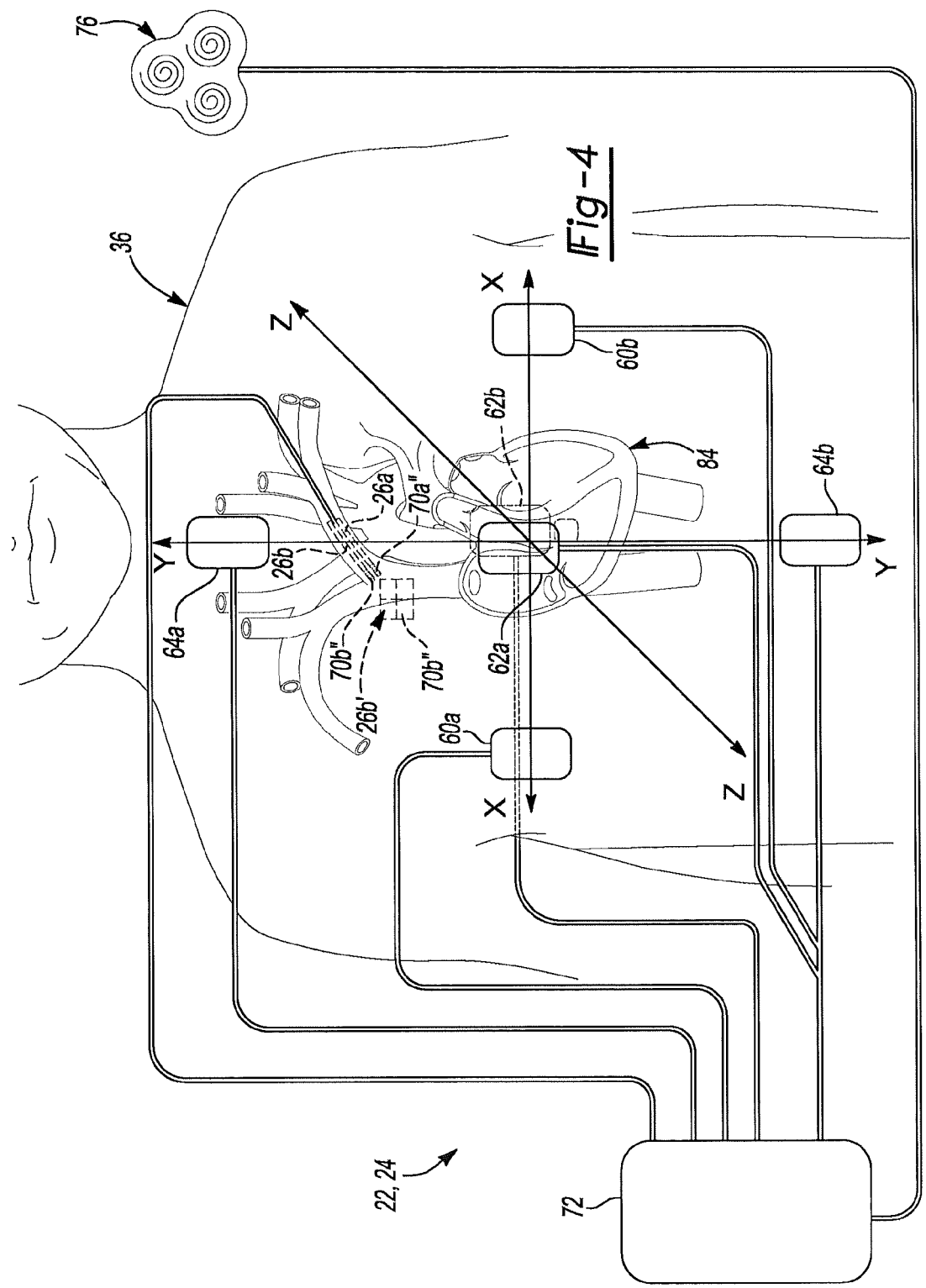
FIG. 4 is an environmental view of a navigation system, according to various embodiments.

With reference to FIG. 4, a tracking device 70" can include an EP tracking device 70a" and an EM tracking device 70b". The EP tracking device 70a" can be positioned on a first instrument portion 26a and the EM tracking device 70b" can be positioned on a second instrument portion 26b. The two instrument portions 26a, 26b can be positioned within the patient 36. Alternately, one of the two instrument portions 26 can be positioned relative to the patient 36 in any appropriate manner. For example, the second instrument portion 26b including the EM tracking device 70b" can be positioned on an exterior surface of the patient 36 or be implanted as a fiducial or dynamic reference frame in the patient 36, such as fixed relative to the heart 84.

The two tracking devices 70a" and 70b" can be moved relative to one another during an operative procedure. For example, if both of the tracking devices 70a" and 70b" are positioned on two separate and moveable instruments 26a, 26b they can be moved to a known position relative to one another within the patient 36 during an operative procedure. Alternatively, if the second instrument 26b is positioned at a fixed location relative to the patient 36, the first instrument portion 26a can be moved to a known position relative to the second instrument portion 26b during an operative procedure. For example, fluoroscopic or ultrasound imaging, such as with the imaging system 30, can be used to confirm or determine the known position of the first surgical instrument 26a and the second instrument 26b. Accordingly, during a second procedure, a position of the EP tracking device 70a" and the EM tracking device 70b" can be determined.

A location of the EP tracking device 70a" can be determined with the EP tracking system 22. The EM tracking system 24 can be used to determine the location of the EM tracking device 70b". As discussed further herein, the determined location of the two tracking devices 70a", 70b" can be used to register the EP tracking system 22 and the EM tracking system 24. The tracked position of the two instruments 26a, 26b can be used for illustration of an icon representing one or both of the instruments 26a, 26b on the display devices 38, 40 relative to the image data 80.

Figure 5:
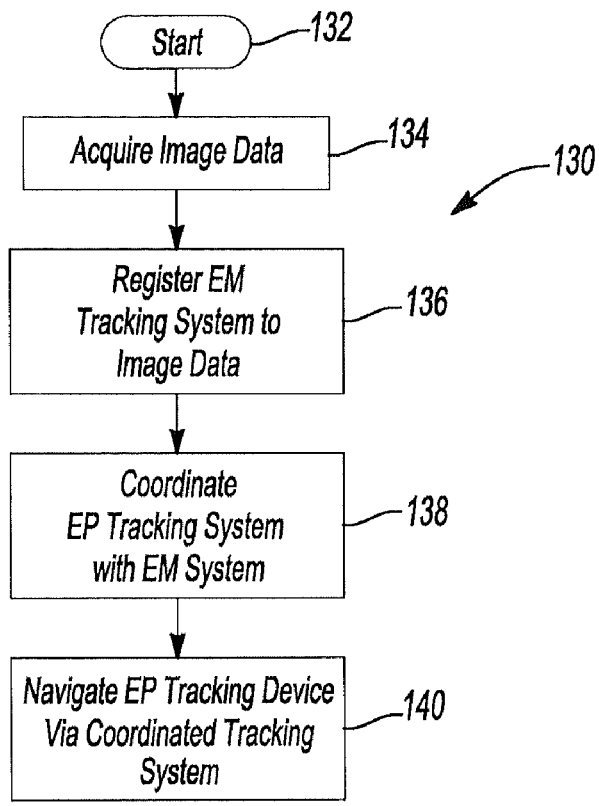
FIG. 5 is a flow chart of a method of registering two navigation systems.

Turning reference to FIG. 5, a flow chart or navigation method for registering or coordinating a dual tracking system 130 is illustrated. The navigation method 130 is illustrated briefly in FIG. 5 and further detailed in FIGS. 7A-7C and 8. The method of using a two tracking system navigation system will be discussed in an exemplary embodiment herein. It will be understood, however, that a navigation system including two or more tracking systems can be used according to various embodiments, including those discussed above. The assembly 92, however, is discussed as an exemplary embodiment.

The navigation method 130, as discussed in detail herein, allows for registration of the EP tracking system 22 to the EM tracking system 24 and further to the image data 80. The EM tracking system 24 can be registered to the image data 80, as discussed herein, including registering the navigation domain of the EM tracking system 24 with the image space. The EP tracking system 22, including the navigation domain of the EP tracking system 22, can be registered to the EM tracking system 24, including the EM navigation domain, according to various embodiments, such as using the devices discussed above. The registration of the EP tracking system 22 to the EM tracking system 24 can allow the EP tracking system 22 to be registered to the image data 80.

The navigation method 130 can include starting in start block 132. The image data 80 can then be acquired in block 134. In addition, with reference to FIG. 6, the image data 80 can be displayed on the display device 40. As discussed above, an icon 92i can be superimposed on the image data 80 to represent a location of an appropriate instrument, such as the surgical instrument 26. The image data 80 can include three dimensional or two dimensional image data that is acquired for representation or illustration of a portion of the patient 36. It will be further understood that the image data 80 acquired in block 134 can be image data that is acquired preoperatively, intraoperatively, or at any appropriate time. It may also include a combination of preoperative and intraoperative image data. For example, preoperative image data can be merged or registered with intraoperative image data according to any appropriate technique. For example, 2D to 3D image registration can occur as described in U.S. patent application Ser. No. 10/644,680 filed Aug. 20, 2003, incorporated herein by reference.

The acquired image data can be stored or transferred to the processor system 44 which is a part of the navigation system 20 for use in illustrating a tracked location of the surgical instrument 26 relative to the patient 36. To assist in illustrating the correct location of the surgical instrument 26 relative to the patient 36, the patient space generally defined by the tracking system 22, 24, can be registered to the image data 80 or image space in block 136. The registration of the image data 80 to the patient space can be with any appropriate method, as discussed above.

The registration of the image data 80 to the patient space can be performed with the EM tracking system 24. The EM tracking system 24, including the localizer 76, can generate a field and navigation space which can be substantially known and definable Euclidean coordinates. The known navigation space can be efficiently and directly registered to Euclidean coordinates of the image data 80. The known field of the EM localizer 76 allows a detected change in the field generated with the EM localizer 76 to be directly related to a distinct position or movement in the field at substantially all points in the field. In other words, a detected changed of movement of the EM tracking device 70b generally equals a selected known movement of the EM tracking device 70b within the field regardless of the position of the EM tracking device 70b within the field generated by the EM localizer 76. Also, every space in the EM navigation domain is known due to the uniform electromagnetic field. Accordingly, a coordinate system identified or defined by the EM tracking system 24 can be substantially known and efficiently applied to the coordinate system of the image data 80.

The registration of the image data 80 to the patient space identified with the EM tracking system 24 can be performed in any appropriate manner. As discussed above, point, contour, or any other appropriate registration processes can be used. For example, the EM tracking device 70b can be positioned relative to known fiducials or landmarks within the patient 36 and similar or correlated landmarks or fiducials can be identified in the image data 80. The processor system 44, or any appropriate processor system, can then be used to register or correlate the points in the image data 80 to the points of the patient space. Once the registration has occurred, the image data 80 is registered to the patient space identified or within the navigation space defined by the EM tracking system 24.

The EM tracking system 24 can be registered to the EP tracking system 22 in block 138. The registration or coordination between the EM tracking system 24 and the EP tracking system 22 can occur at any appropriate time, such as before or after the EM tracking system 24 is registered to the image data in block 136. The EP tracking system 22 can be registered to the EM tracking system 24 in block 138 in any appropriate manner. As discussed further herein, exemplary registration systems 138a, 138b, and 138c are illustrated and described in greater detail in relation to FIGS. 7A-7C. Once the EP tracking system 22 is registered with the EM tracking system 24, navigation of the instrument 26 with only the EP tracking device 70a can be done in block 140. The navigation with the EP tracking device 70a can be done and a position of the instrument 26 including the tracking device 70a can be navigated relative to the image data 80 due to the registration of the EP tracking system 22 and the EM tracking system 24 in block 138. Accordingly, navigation using only the EP tracking system 22 can occur in block 140.

Figure 7A:
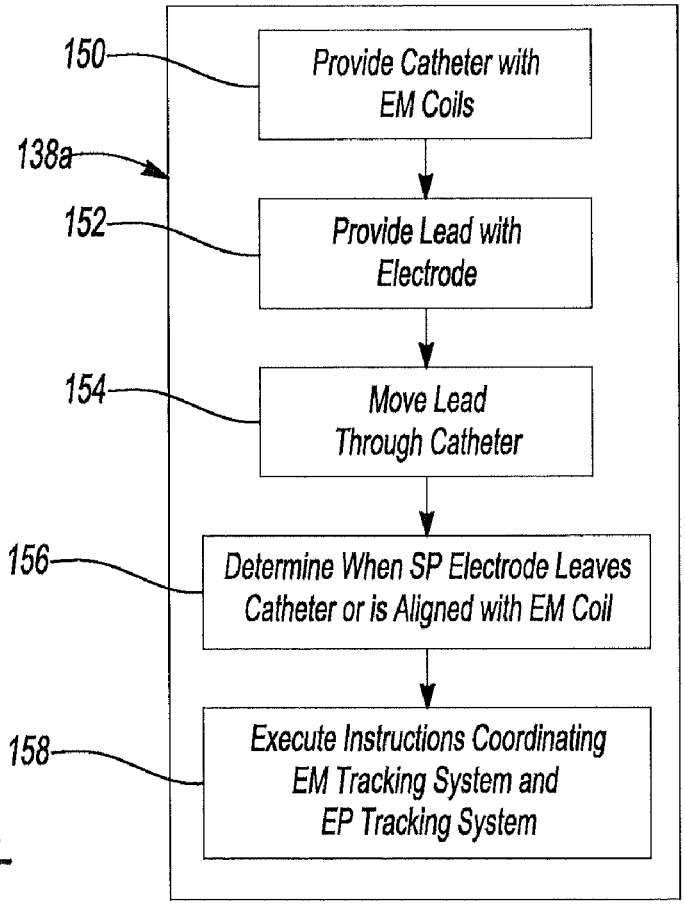
FIG. 7A-7C are detailed flowcharts of registration of two tracking systems.
Figure 6:
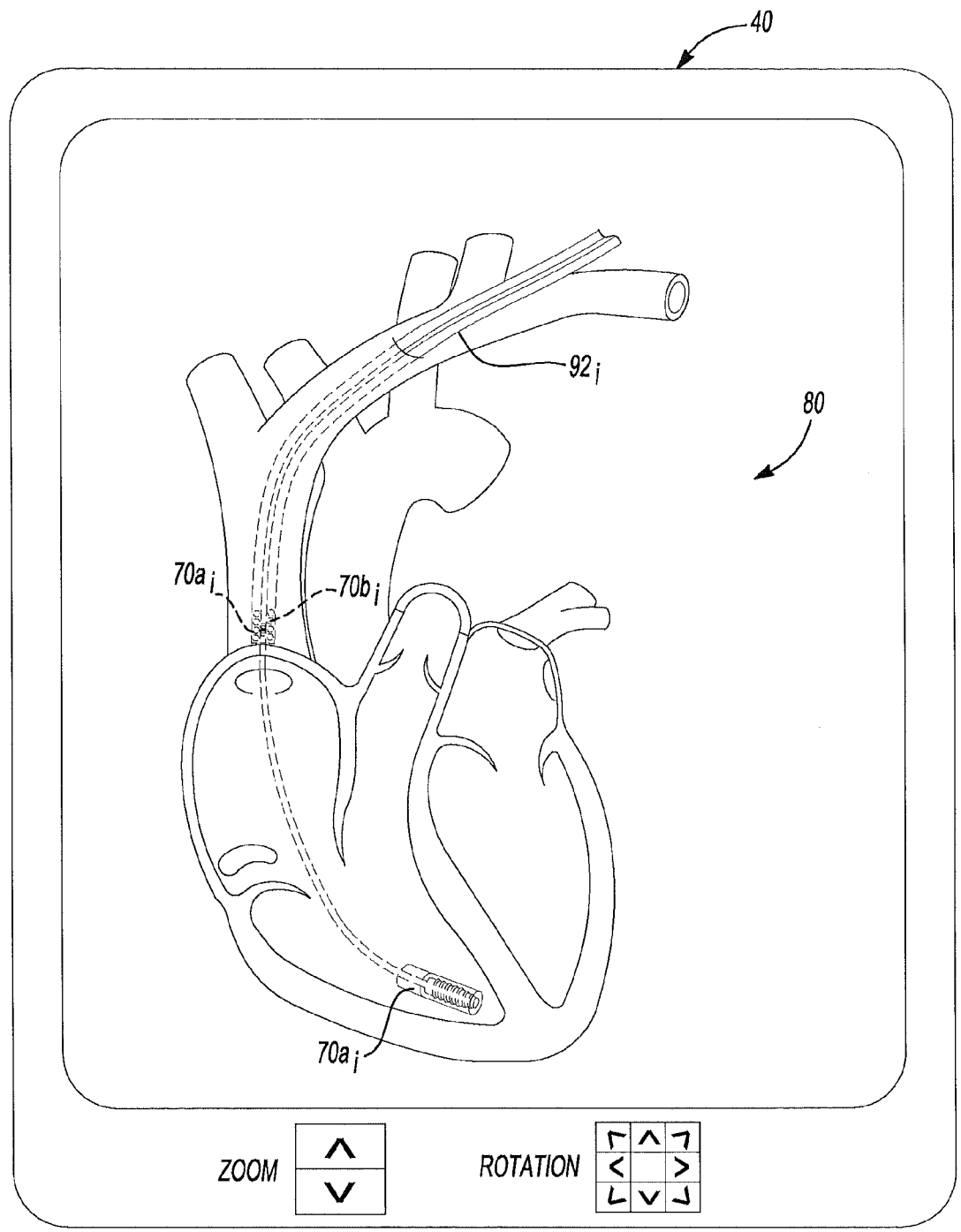
FIG. 6 is a view of image data and icons displayed relative to the image data, according to various embodiments.

With continuing reference to FIGS. 5 and 6 and additional reference to FIG. 7A, registration of the EM tracking system and the EP tracking system, according to various embodiments, is illustrated in block 138a. As discussed above, the lead assembly 92 can include the EP tracking device 70a that can be defined by the tip electrode 90 of the lead 92. The catheter 100 can include one or more coils 102, 104 of the EM tracking device 70b. As illustrated in FIG. 6, the EM tracking device 70b can be used to register the image data 80 to the patient space of the patient 36.

Once the registration has occurred in block 136, then the EP tracking system 22 can be registered with the EM tracking system 24 in block 138a, illustrated in FIG. 7A. A lead or instrument including an EP electrode can be provided in block 152. The EP electrode can be a distal tip electrode of the lead or can be provided in any other portion, such as in the sheath 94. For example, as illustrated in FIG. 2A, the alternative EP tracking device 70a' can be provided in the sheath 94. Regardless of the position of the electrode it can be used as the EP tracking device 70a and it can be positioned relative to the EM tracking device 70b that is positioned within the catheter 100. In addition, as illustrated in FIG. 2B, the lead including the EP tracking device 70a can be moved relative to the catheter 100 in block 154.

When moving the lead relative to the catheter 100, it can be determined when the EP tracking device 70a moves past or is near the coils 102, 104 of the EM tracking device 70b in block 156. Various mechanisms can be used to determine when the EP electrode 70a moves past the EM tracking device 70b. For example, a change in impedance, measured voltage, or other determinations can be used to determine when the EP electrode is next to or immediately past the EM tracking device 70b.

When the determination is made that the EP tracking device 70a has been positioned relative to the EM tracking device 70b, such as substantially in the same position, a registration of the EM tracking system 24 and the EP tracking system 22 can occur in block 158. The registration can occur by substantially coordinating or registering the EP tracking system 22 and the EM tracking system 24. In other words, because the EP tracking system 22 can be used to determine the position of the EP tracking device 70a and the EM tracking system 24 can be used to determine the position of the EM tracking device 70b these two positions or points in patient space can be identified as the same. Accordingly, the navigation space of the EP tracking system 22 can be overlaid or registered with the navigation space of the EM tracking system 24.

The coordination or registration between the EP tracking system 22 and the EM tracking system 24 can be performed by acquiring a selected number of points that are identical or at known locations relative to one another, as discussed above, with both of the tracking systems. For example, at least three corresponding points may be acquired though more points may be used to actually model or characterize the non-orthogonal or known navigation space defined by the EP tracking system 22. Less information may be necessary in a local or small region than would be needed for a larger space, such as an entire navigation space. Once points with both of the tracking systems have been acquired a curvature model, such as a spline model, can be used to model the EP tracking system 22 coordinate system or navigation space. Other appropriate modeling calculations could also be used to computationally coordinate the EP tracking system 22 and the EM tracking system 24.

Once the EM tracking system 24 and the EP tracking system 22 have been registered, movement of the EP tracking device 70a within the patient space of the patient 36 can be illustrated superimposed on the image data 80. As illustrated in FIG. 6, icons illustrating the first tracking device 70ai and second tracking device 70bi can be illustrated and superimposed on the image data 80. Once registration has occurred, however, the EP tracking device icon 70ai, illustrating the position of the EP tracking device 70a, can be illustrated separate from the EM tracking device icon 70bi, representing the position of the EM tracking device 70b, but correctly related to the image data 80. It will be understood that an icon 92i can represent generally the surgical instrument 26, or any portion thereof, and not only the tracking devices. The position of the surgical instrument, however, can be identified or determined based upon the tracked position of the tracking device 70.

Registration of the EP tracking system 22 with of the second navigation space, such as that of the EM tracking system 24, can allow for image navigation of the instrument 26 tracked with only the EP tracking system 22. The navigation space of the EP tracking system 22 may not be substantially uniform or strictly aligned with the image data 80. For example, the tissue of the patient 36 may not be substantially uniform impedance. For example, the impedance of muscle tissue may be substantially different from the impedance of blood or other electrolyte. Accordingly, a particular change in voltage may not always be related to a single physical movement amount of the EP tracking device 70a. Movement of the EP tracking device 70a within the patient 36, however, can be measured using the EP tracking system 22 once it is registered with a tracking system, such as the EM tracking system 24, which can be registered to the image data 80. A registered position of the EP tracking device 70a can be superimposed on the image data 80. Therefore, a position of the EP tracking device 70a can be superimposed on the image data 80 even if a non-uniform navigation space is generated with the EP tracking system 22.

Returning reference to FIG. 7B, registering the EP tracking system 22 and the EM tracking system 24 can be achieved with registration method 138b. According to the registration method 138b, a catheter can be provided with an EP electrode as the EP tracking device 70a in block 170. A lead assembly can be provided with the EM tracking device 70b in block 172. The lead can then be moved relative to the catheter in block 174. A determination can be made when the EM tracking device 70b is aligned with or at a selected and known position relative to the EP tracking device 70a in block 176. A registration of the EM tracking system 24 and the EP tracking system 22 can then occur in block 178. The registration method 138b can be substantially similar to the registration method 138a (illustrated in FIG. 7A) save that the EP electrode is positioned in the catheter 100 and the EM tracking device 70b is positioned on the lead. Therefore, registration can occur in substantially the same way and tracking of the EP tracking device 70a can occur and superimposition of a position of the EP tracking device 70a can be illustrated relative to the image data 80.

Figure 7B:
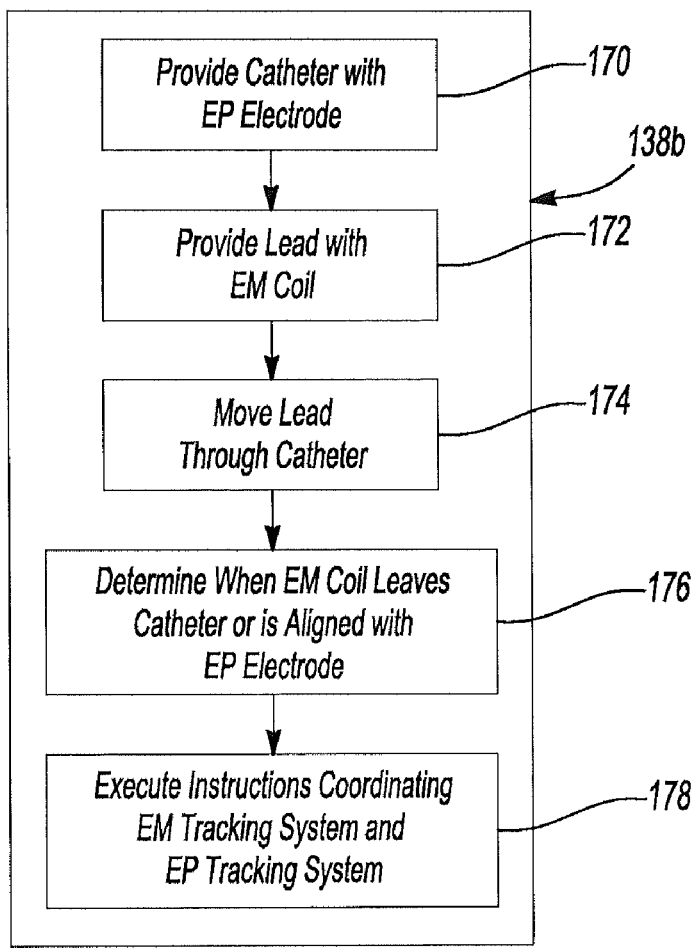
Figure 7C:
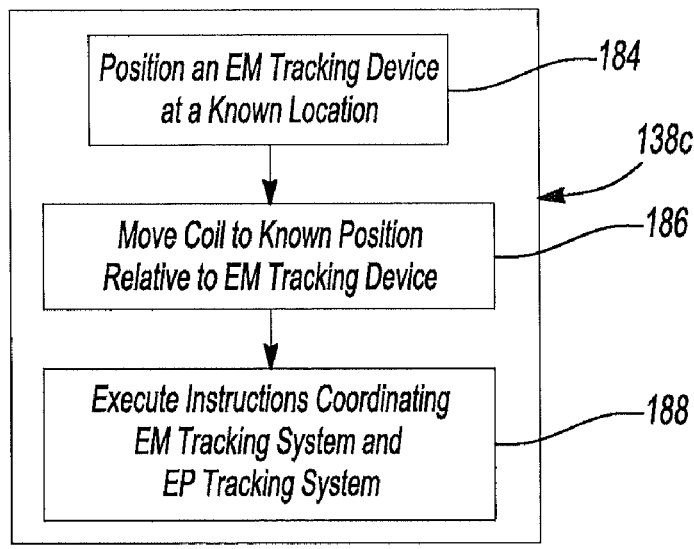

Turning to FIG. 7C, a registration method 138c is illustrated. The registration method 138c can include positioning the EM tracking device 70b at a known location in the patient 36 or other navigable space in block 184. The EM tracking device 70b can be any appropriate device, for example the second tracked instrument 26b illustrated in FIG. 4. The second tracked device 26b can be a second instrument moved relative to the patient 36, a dynamic reference frame fixed relative to the patient 36, or any appropriate device including the EM tracking device 70b. For example, the DRF 26b' can be positioned relative to the patient 36 at a fixed and known location. The known location of the DRF 26b' can be determined in any appropriate manner. For example, a registration probe (not illustrated) can be moved relative to the DRF 26b' to determine the location of the DRF 26b'. In addition, the DRF 26b' can be positioned or include a fiducial that is identified in the image data 80 to allow for identification and registration to the image data 80. Alternatively, if the second instrument 26b is a moveable instrument, it can be moved to a landmark that can also be identified within the image data 80.

When the second tracked device 26b, 26b' is identified relative to the image data 80 and the EM tracking system 24 is registered to the image data 80, the first tracked instrument 26a including the EP tracking device 70a can be moved relative to the second tracked device 26b, 26b'. For example, the first instrument 26a, illustrated in FIG. 4, can move to the location of the DRF 26b' in block 186. Once the first tracked instrument 26a is at the same position as the DRF 26b', registration of the EM tracking system 24 and the EP tracking system 22 can occur in block 188. As discussed above, the location of the two tracking devices 70a, 70b can be determined to be substantially identical when they are positioned next to each other to allow for registration of the two tracking systems 22, 24.

It will be further understood that when two tracked instruments 26a, 26b are provided, they can be positioned at a known position and orientation relative to one another to allow for registration to occur in block 188. For example, it will be understood, the first tracked instrument 26a can be positioned at a known position and orientation relative to the DRF 26b' and registration can occur. In other words, knowing a position and orientation of the DRF 26b' and position and orientation of the EP tracking device 70a can allow for registration of the two tracking systems 22, 24 even if the two tracking devices 70a, 70b are not in substantially identical locations. As discussed above, imaging systems can be used to determine or identify the known locations of the two tracking devices 70a, 70b.

Registration of the EP tracking system 22 and the EM tracking system, 24 can also occur by providing the EP tracking device 70a and the EM tracking device 70b substantially at the same position on the tracked instrument 26, as illustrated with the instrument 120 in FIG. 3. When the tracking device 70 has substantially only one location for both the EP tracking system 22 and the EM tracking system 24 a determination of registration is not otherwise required, including positioning the EP tracking device 70a relative to the EM tracking device 70b. Rather, the tracked position of the EM tracking device 70b with the EM tracking system 24 can be used to correlate the position of the EP tracking device 70a inherently since all positions determined with the EM tracking device 70b are inherently registered with the EP tracking device 70a. Therefore, the coordinate system of the EM tracking system 24 can be used to illustrate a position of the EP tracking device 70a on the image data 80 at all times. This can allow or be used to acquire more than one point that is the same position with both of the tracking devices 70a and 70b. This can assist in registration of the EP tracking system 22 and the EM tracking system 24. It will be understood, however, that the two tracking devices 70a and 70b need not be the same device to acquire more than one point that is at the same position with both of the tracking devices 70a and 70b.

Even when the two tracking devices 70a, 70b are the same device or formed to be at the same or fixed relative positions, a third tracking device can be provided. For example, the tip electrode 92 can also be interconnected with the controller 72. Thus, the position of the tip electrode 92 can be tracked once it has exited the catheter 122.

In addition, or alternatively, it will be understood that the EP tracking device 70a and the EM tracking device 70b need not be positioned on top of one another, but can be positioned substantially at a known fixed location relative to one another or next to each other with a selected assembly. For example, an electrode of the EP tracking device 70a can be positioned substantially abutting coils of wire defining the EM tracking device 70b. They can also be positioned a distance from one another at a substantially known location, at least when a device is at a known configuration. The known relationship or relative positions of the EP tracking device 70a and the EM tracking device 70b can be used to register the EP tracking system 22 and the EM tracking system 24 even if the EP tracking device 70a and the EM tracking device 70b are not at the same location.

Figure 8:
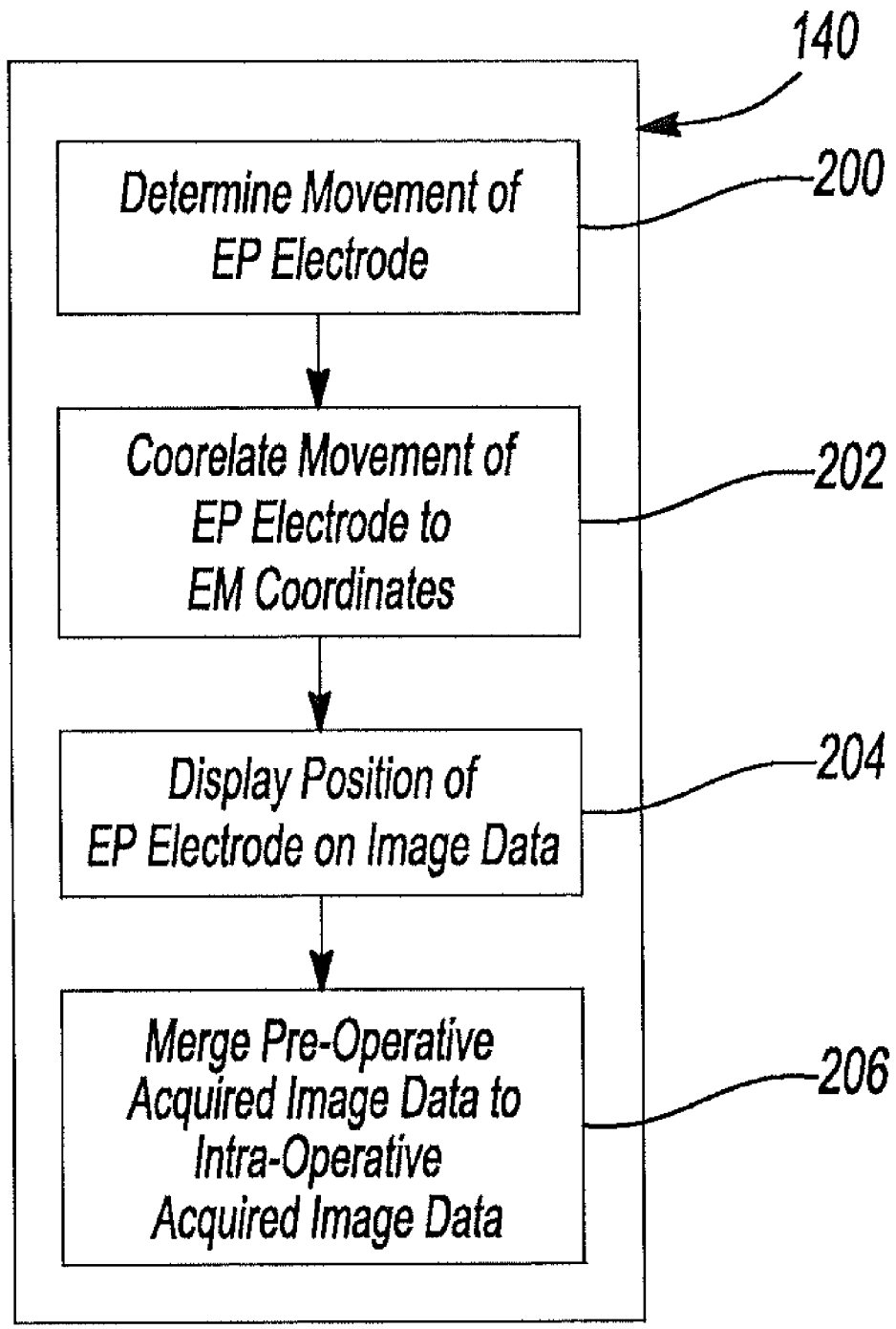
FIG. 8 is a detailed view of navigating a registered instrument.

Turning to FIG. 8, navigating the EP tracking device 70a in block 140 is described in further detail. Movement of the EP tracking device 70a can be determined in block 200. The movements of the EP tracking device 70a can then be registered to the coordinates of the EM tracking system 24 in block 202. As discussed above, registration of the EP tracking system 22 and the EM tracking system 24 allow for a registration of a coordinate in the EM tracking system 24 with a determined position of the EP tracking device 70a in the EP tracking system 22.

Because of the registration of the EP tracking system 22 and the EM tracking system 24, a position of the EP tracking device 70a can be illustrated or displayed on the display device 38, 40 in block 204. As discussed above regarding FIG. 6, a tracked position of just the EP tracking device 70a with the EP tracking system 22 can be displayed on the display device 40 relative to the image data 80. For example, the icon 70ai representing a position of the instrument tracked with the EP tracking device 70a can be displayed on the image data 80.

Merging preoperative acquired image data, such as the image data 80, can be done to intraoperative acquired image data in block 206. The merging of the image data can occur in any appropriate manner. One appropriate method can include contour merging, which matches contours in the preoperative acquired image data and intraoperative acquired image data. For example, if image data of a vertebra is acquired preoperatively and contours of a vertebra is acquired intraoperatively they can be matched. The contours can be manually or automatically determined in the image data and matched between image data sets.

Additionally, tracking the EP tracking device 70a can be used to create point clouds for various organs. For example, a point cloud or point cloud map can be generated for a portion of the heart 84. The point cloud can then be matched, such as with contour matching or landmark matching, with preoperative acquired image data. Point cloud matching or generation includes identifying one or more points with the tracking device 70, such as with the EP tracking device 70a to generate a surface of a volume. Appropriate cloud mapping techniques include those described in U.S. patent application Ser. No. 12/117,537, filed on May 8, 2008, incorporated herein by reference. It will be understood, however, that the generation of the point cloud can be made with either the EP tracking device 70a or the EM tracking device 70b. However, the EP tracking device 70a, which can include an electrode, can be provided at a selected size, such as one that will easily maneuver within the heart 84 to allow for an efficient generation of the cloud map by identifying a plurality of points. Accordingly, a selected one of the tracking devices 70a, 70b can be efficiently used to generate a selected type of data, such as a landmark or cloud map, for merging of intraoperative and preoperative image data.

In addition, the electrode 92 of the lead 90 can be used as the EP tracking device 70a. The tip electrode 92 can be implanted in the heart 84. Accordingly, image data 80, which can be pre- or intra-operatively acquired, can be used to identify or suggest a selected location of the lead tip 92. By correlating the EM tracking system 24 and the EP tacking system 22 a selected location identified relative to the image data 80 can be used to guide the electrode 92 to an appropriate or selected location for implantation. An additional tracking device, such as the EM tracking device 70b, is not required to track the electrode 92 to a selected location within the heart 84 with the image data 80 because of the registration of the EM tracking system 24 and the EP tracking system 22. Suggesting a placement of a lead tip can be based on any appropriate information, such as historical data, statistical data, or atlas models. Exemplary suggestion systems include those disclosed in U.S. Patent Application Publication No. 2002/0097806, published on May 20, 2004, incorporated herein by reference.

Providing registered tracking systems can be used for various purposes. As discussed above, the EM tracking system 24 and the EP tracking system 22 can be used for different tracking purposes or in different locations. In addition, the EP tracking system 22 may not generate an appropriate signal in various portions of the patient 36. For example, if the EP tracking device 70a is not positioned within a portion of the patient 36 that includes an electrolyte or appropriately conducted material, a voltage may not be generated relative to the EP tracking device 70a when a current is induced in the patient 36. Therefore, the EM tracking device 70b can be used to track the position of the instrument 26 relative to the patient 36.

According to various embodiments, the EP tracking device 70a can be substantially smaller than the EM tracking device 70b. For example, the EP tracking device 70a may only include a single wire or small conductive member to act as an electrode. The small dimensions of the electrode of the EP tracking device 70a and can allow it to move to selected locations, such as within the heart 84, which may not be accessible with a larger tracking device, such as the EM tracking device 70b. Therefore, providing the EP Tracking system 22 and the EM tracking system 24 can allow for tracking the surgical device 26, or any appropriate device, with more than one modality.

The EP tracking system 22 can be used to track the lead electrode 90 as the EP tracking device 70a. Accordingly, the EP tracking system 22 can be used to track the location of the lead electrode 90 to its intended implantation site or location with the EP tracking device 70a. The tracked position can then be displayed on the display devices 38, 40 for viewing by the surgeon 34.

The EP tracking system 22, however, may not be directly registerable to the image data 80. As discussed above, varying impedances of tissue of the patient 36 may inhibit registration of the EP tracking system 22 with the image data 80. Lack of registration with the image data 80 can reduce effectiveness of image navigation.

The EM tracking system 24, however, can be registered with the image data 80. The EM tracking system 24, including the more uniform navigation domain, can be registered to the image data 80. In determining one or more points, also referred to as identity points, in both the EP tracking system 22 navigation domain and the EM tracking system 24 navigation domain the two tracking systems can be registered. This can allow the EP tracking system 22 to be registered to the image data 80. Registration can also allow the use of pre-acquired image data that can be registered to intraoperative image data or other appropriate image data for navigation of the instrument 26 with the EP tracking device 70a.

In addition, the two tracking systems 22, 24 can be used for complimentary purposes. For example, the EM tracking system 24 may have a higher accuracy than the EP tracking system 22. Therefore the EM tracking system 24 can be used to determine locations of various landmarks for registration, while the EP tracking system 22 is used for navigation of the instrument 26 for implantation. Also, if location and size permits, the EM tracking system 24 can be used to confirm a location of the instrument 26 after implantation.

Further, the EM tracking system 24 can track the tracking device 70b in the absence of a conductive material. Thus, the EP tracking device 70a can be used to track the instrument when a conductive medium and current is present (e.g. within the heart 84) and the EM tracking device 70b can be used to track the instrument 26 when the conductive medium is not present (e.g. exterior to the heart 84).

It will be further understood that the tracking systems 22, 24 can be used to track any appropriate device relative to any appropriate volume. For example, positioning a device within an enclosed volume may be selected for building, manufacturing, or repairing various workpieces in selected workspaces. For example, a device can be moved relative to an enclosed volume, such as within an airplane, robot, or other enclosed areas without requiring open visualization or access within the volume. The enclosed volume of the workpiece or workspace, may also include more than one type of environment. Accordingly, having multiple tracking systems using differing tracking modalities can be used to track a single instrument or two parts of the single instrument within any appropriate volume.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system for tracking an instrument within a volume, comprising:
   a first electromagnetic tracking system including a first tracking device operable to determine a position of the first tracking device within a first tracking domain;
   a second electropotential tracking system including:
      a plurality of current electrodes operable to induce a current into the volume to form a second tracking domain;
      a second tracking device operable to sense a voltage at the second tracking device based upon the induced current;
   an instrument having a first portion connected to the first tracking device and a second portion connected to the second tracking device to allow tracking of the instrument with at least one of the first tracking system or the second tracking system, wherein the second portion is operable to move relative to the first portion to place the second tracking device at a known position relative to the first tracking device;

a controller in communication with the first electromagnetic tracking system and the second electropotential tracking system;

wherein the controller is operable to determine a registration of the first tracking domain and the second tracking domain based on at least the position of the first tracking device relative to the second tracking device within the volume;

wherein the registration is operable to allow tracking of the instrument with either of the first electromagnetic tracking system or the second electropotential tracking system in the volume.

2. The system of claim 1, further comprising:

an imaging system operable to acquire image data of the volume;

wherein the first electromagnetic tracking system is operable to generate an electromagnetic field defining a tracking volume domain of a determined uniformity within the volume allowing the first tracking domain to be registered to the image data.

3. The system of claim 2, wherein the first electromagnetic tracking system includes a localizer;

wherein either of the localizer or the first tracking device is operable to generate the electromagnetic field and the other of the localizer or the first tracking device is operable to sense the electromagnetic field;

wherein the electromagnetic field defines the first tracking domain.

4. The system of claim 2, wherein the imaging system is operable to acquire image data of the first tracking device and the second tracking device to determine the position of the first tracking device and the second tracking device relative to each other within the volume.

5. The system of claim 1, wherein the instrument having the first portion and the second portion includes:

an outer member as the first portion and an inner member as the second portion, wherein the outer member and the inner member are operable to move relative to one another;

wherein the outer member is connected to the first tracking device and the second inner member is connected the second tracking device.

6. The system of claim 1, wherein the first tracking device is configured to be fixedly associated with the volume;

wherein the second tracking device is moveable to a known position relative to the first tracking device;

wherein when the second tracking device is at the known position, the controller is operable to correlate the position of the first tracking device relative to the second tracking device and correlate the first tracking domain relative to the second tracking domain.

7. The system of claim 1, wherein the instrument is a catheter and lead assembly;

wherein the catheter includes a first tracking device and the lead includes the second tracking device.

8. The system of claim 7, wherein the first tracking device is one or more coils of wire and the second tracking device includes an electrode.

9. The system of claim 1, wherein the first tracking device and the second tracking device are formed as a single device operable to be tracked within both of the first electromagnetic tracking system and the second electropotential tracking system.

10. The system of claim 9, wherein the single device includes a first portion defining an electrode to sense a voltage and a second portion operable to sense or generate a field.

11. The system of claim 1, wherein the instrument includes both the first tracking device and the second tracking device operable to be positioned at a known position relative to one another in at least a first orientation of the instrument.

12. The system of claim 1, wherein the instrument includes a lead having an electrode;

wherein the electrode of the lead is the second tracking device.

13. A method of tracking an instrument using at least a first tracking system and a second tracking system, comprising:

providing the first tracking system to determine a position of a first tracking device, including:

generating an electromagnetic field to define a first navigation space in a volume;

determining a first position of the first tracking device with the generated electromagnetic field;

providing the second tracking system to determine a position of a second tracking device, including:

generating a current in the volume to define a second navigation space;

sensing a voltage with the second tracking device;

determining a second position of the second tracking device based upon the sensed voltage;

registering the first tracking system and the second tracking system based upon moving the second tracking device to a known position relative to the first tracking device; and tracking the second tracking device with the second tracking system and illustrating on a display device a position of the second tracking device based upon the registration of the first tracking system and the second tracking system.

14. The method of claim 13, further comprising:

providing image data of the volume;

registering the image data to the first navigation space; and illustrating on the display device the determined first position of the first tracking device.

15. The method of claim 14, wherein moving the second tracking device to a known position relative to the first tracking device includes:

positioning the first tracking device on a tube;

moving the second tracking device through the tube; and measuring a signal change when the second tracking device moves past the first tracking device.

16. The method of claim 14, wherein registering the first tracking system and the second tracking system, includes:

determining a first identity position in the volume with the first tracking device in the first navigation space;

determining a second identity position in the volume with the second tracking device in the second navigation space;

relating a selected plurality of points in the second navigation space with a selected plurality of points in the first navigation space based upon the known first identity position and the second identity position;

calculating a position with the second tracking system of the second tracking device once the second tracking device is no longer at the identity position; and displaying a tracked position of the second tracking device on the display device relative to the image data.

17. The method of claim 16, wherein determining the first identity position includes determining a plurality of first identity positions and determining a second identity position includes determining a plurality of second identity positions; and registering the first tracking system and the second tracking system based on the determined plurality of first identity positions and plurality of second identity positions.

18. The method of claim 17, wherein determining a first identity position includes positioning the first tracking device at substantially the same location as the second tracking device.

19. The method of claim 16, wherein determining the first position of the first tracking device and the second position of the second tracking device includes:
acquiring image data of the first tracking device and the second tracking device; and
determining spatial positions of both the first tracking device and the second tracking device in the image data.

20. The method of claim 16, further comprising:
selecting a position to implant a lead; and
navigating a lead with the image data based upon the tracked position of the second tracking device alone.

21. The method of claim 16, further comprising:
illustrating a selected position of implantation for a lead on the image data; and
navigating a lead to the selected position while substantially only tracking the position of the second tracking device.

22. The method of claim 13, further comprising:
providing a catheter including the first tracking device; and
providing a lead including the second tracking device.

23. The method of claim 13, further comprising:
providing a lead including the second tracking device;
wherein the lead includes an electrode as the second tracking device.

24. A system for tracking an instrument including a tracking device operable to be tracked within a volume, comprising:
a tracking device including:
a tip electrode,
an annular ring electrode, and
a coil of conductive material wrapped relative to a surface of the annular ring; and
a first electromagnetic tracking system for determining a position of the coil of conductive material within a first tracking domain;
a second electropotential tracking system including:
a plurality of current electrodes operable to induce a current into the volume to form a second tracking domain;
wherein the tip electrode and the annular ring electrode are operable to sense a voltage based upon the induced current;
a communication system interconnecting the tip electrode, the annular ring and the coil of conductive material with both the first tracking system and the second tracking system;
an instrument having a first portion connected to the tip electrode and a second portion connected to the annular ring electrode and the coil of conductive material to allow tracking of the instrument with at least the second tracking system, wherein the second portion is operable to move relative to the first portion to place the annular ring electrode at a known position relative to the tip electrode;
a controller in communication with the first electromagnetic tracking system and the second electropotential tracking system;
wherein the controller is operable to determine a registration of the first tracking domain and the second tracking domain based on at least the position of the annular ring relative to the coil of conductive material within the volume;
wherein the registration is operable to allow tracking of the first portion with the second electropotential tracking system in the volume.

25. The system of claim 24, wherein the first electromagnetic tracking system includes:
a first localizer operable to generate an electromagnetic field or sense an electromagnetic field;
wherein the coil of conductive material is operable to generate an electromagnetic field or sense an electromagnetic field.

26. The system of claim 24, further comprising:
a display device;
wherein the first or second tracking system is in communication with the display device and operable to display a represented position of the annular ring, the coil of conductive material, or combinations thereof.

27. The system of claim 26, wherein image data is operable to be displayed on the display device relative to the representation of the annular ring and the coil of conductive material.

28. The system of claim 24, further comprising:
wherein the second portion defines a cannula and the annular ring and coil of conductive material are positioned around the cannula.

29. The system of claim 28, wherein the instrument includes at least one of a catheter, an implantable lead, or combinations thereof.

* * * * *